US012668568B2

(12) United States Patent
Kassiou et al.

(10) Patent No.: US 12,668,568 B2
(45) Date of Patent: Jun. 30, 2026

(54) ADAMANTANYL-SUBSTITUTED BENZAMIDE COMPOUNDS AND THEIR USE AS P2X$_7$ RECEPTOR ANTAGONISTS

(71) Applicant: The University of Sydney, Sydney (AU)

(72) Inventors: Michael Kassiou, Lugamo (AU); Gemma Figtree, Sydney (AU); James O'Brien-Brown, Lane Cove North (AU); Shane Wilkinson, Sydney (AU); Thomas Hansen, Greenwich (AU)

(73) Assignee: THE UNIVERSITY OF SYDNEY, Sydney (AU)

( * ) Notice: Subject to any disclaimer, the term of this patent is extended or adjusted under 35 U.S.C. 154(b) by 774 days.

(21) Appl. No.: 17/269,244

(22) PCT Filed: Aug. 24, 2018

(86) PCT No.: PCT/AU2018/050905
§ 371 (c)(1),
(2) Date: Feb. 17, 2021

(87) PCT Pub. No.: WO2020/037350
PCT Pub. Date: Feb. 27, 2020

(65) Prior Publication Data

US 2021/0323910 A1 Oct. 21, 2021

(51) Int. Cl.
*C07C 235/60* (2006.01)
*A61P 25/28* (2006.01)

(52) U.S. Cl.
CPC ............ *C07C 235/60* (2013.01); *A61P 25/28* (2018.01); *C07C 2603/74* (2017.05)

(58) Field of Classification Search
CPC ..... C07C 235/60; C07C 2603/74; A61P 25/28
See application file for complete search history.

(56) References Cited

FOREIGN PATENT DOCUMENTS

| | | | | | |
|---|---|---|---|---|---|
| EP | 870757 | A2 * | 10/1998 | .......... | C07C 211/38 |
| WO | 1998/040337 | A1 | 9/1998 | | |
| WO | 1999/029661 | A1 | 6/1999 | | |
| WO | WO-9929661 | A1 * | 6/1999 | .......... | C07C 233/65 |
| WO | 2008/064432 | A1 | 6/2008 | | |
| WO | 2014/060586 | A1 | 4/2014 | | |
| WO | 2020/037350 | A1 | 2/2020 | | |

OTHER PUBLICATIONS

S. Wilkinson, et al. Pharmacological Evaluation of Novel Bioisosteres of an Adamantanyl Benzamide P2X7 Receptor Antagonist, ACS Chemical Neuroscience Aug. 2017 (11), 2374-2380 DOI:10.1021/acschemneuro.7b00272. (Year: 2017).*

By G. Anderson, et al. Novel Synthesis of 3-Fluoro-1-Aminoadamantane and Some of its Derivatives, Synthetic Communications, 1988, VL-18, IS-16-17, pp. 1967-1974, doi: 10.1080/00397918808068263. (Year: 1988).*

B. Janssen et al. (Scientific Reports (Apr. 2018) 8:6580, DOI:10.1038/s41598-018-24814-0. (Year: 2018).*

N. Meanwell (J. Med. Chem. Feb. 2018, 61, 14, 5822-5880, doi.org/10.1021/acs.jmedchem.7b01788. (Year: 2018).*

J. Wang et al. (Chem. Rev. 2014, 114, 4, 2432-2506, doi.org/10.1021/cr4002879. (Year: 2014).*

Wilkinson et al., Pharmacological Evaluation of Novel Bioisosteres of an Adamantanyl Benzamide P2X7 Receptor Antagonist. ACS Chemical Neuroscience, vol. 8, pp. 2374-2380 (2017).

Stepanov et al., Interaction of 3,7-dimethylenebicyclo [3.3.1]nonane with perbenzoic and monoperphthalic acids. Zhurnal Organicheskoi Khimii, vol. 8, pp. 1179-1183 (1972).

Anderson et al., Novel Synthesis of 3 Fluoro-1-amindoadamantane and Some of its Derivatives. Synthetic Communications, vol. 18, pp. 1967-1974 (1988).

CAS Registry No. 1347899-81-3 , STN Entry date Dec. 4, 2011, Benzamide, 3-chloro N-[3-chlorotricyclo [3.3.1.13, 7]dec-1-yl)methyl] Database CAS Dec. 4, 2011 (Dec. 4, 2011), "Benzamide, 3-chloro-N-[(3-chlorotricyclo[3.3.1.13,7]dec-1-yl) methyl", retrieved from STN Database accession No. 1347899-81-3.

CAS Registry No. 519046-36-7, STN Entry Date May 22, 2003, Benzamide, N-[(3-chlorotricyclo[3.3.1.13,7]dec-1-yl)methyl]-4-methoxy.

International Search Report and Written Opinion, mailed Sep. 19, 2018, for International Application No. PCT/AU2018/050905 filed on Aug. 24, 2018.

* cited by examiner

*Primary Examiner* — James H Alstrum-Acevedo
*Assistant Examiner* — Manahil Mirghani Ali Abdalhameed
(74) *Attorney, Agent, or Firm* — Bryan D. Zerhusen; Nicholas R. Herrel; CANTOR COLBURN LLP

(57) ABSTRACT

The present invention relates to adamantanyl-substituted benzamide compounds and their use as antagonists of the P2X$_7$ purinoreceptor. The invention further relates to methods for the treatment of disease and conditions associated with the P2X$_7$ purinoreceptor.

12 Claims, 7 Drawing Sheets

(A)

(B)

ADAMANTANYL-SUBSTITUTED BENZAMIDE COMPOUNDS AND THEIR USE AS $P2X_7$ RECEPTOR ANTAGONISTS

FIELD OF THE INVENTION

The present invention broadly relates to adamantanyl-substituted benzamide compounds and their use as antagonists of the $P2X_7$ purinoreceptor.

BACKGROUND OF THE INVENTION

The $P2X_7$ purinoreceptor ($P2X_7R$) is a non-selective, ligand-gated cation channel ubiquitously expressed on many immune cells, including microglial cells in the Central Nervous System (CNS). It is up-regulated in response to pro-inflammatory stimuli and has been implicated in a number of neuroinflammatory diseases. Activation of the $P2X_7R$ by the extracellular nucleotide adenosine triphosphate (ATP) mediates the processing and release of the pro-inflammatory cytokine, interleukin 1β (IL-1β), which is involved in a variety of cellular actions including cell proliferation, differentiation and apoptosis. Furthermore, the $P2X_7R$ is involved in caspase activation as well as in the induction of apoptosis. Pharmacological inhibition and genetic studies of the $P2X_7R$ have shown elimination or reduction of symptoms in animal models of arthritis, depression, neuropathic pain, multiple sclerosis and Alzheimer's disease. The modulation of $P2X_7R$ activity through the development of $P2X_7R$ antagonists appears to be a viable strategy for the treatment of neuroinflammatory diseases. Numerous drug classes have been identified in the pursuit to discover selective $P2X_7R$ antagonists, however very few have proceeded to clinical trials.

Against this background the present inventors have developed potent $P2X_7R$ antagonists possessing favourable pharmacokinetic properties and efficacy across several polymorphs of human $P2X_7R$. The new compounds may find use in the treatment of diseases and conditions associated with $P2X_7R$.

SUMMARY OF THE INVENTION

In a first aspect the present invention provides a compound of the general formula (I):

(I)

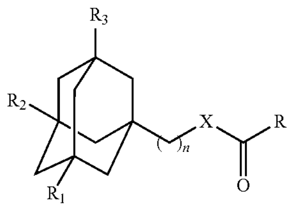

or a pharmaceutically acceptable salt, hydrate, derivative, solvate, tautomer or prodrug thereof, wherein:

$R_1$, $R_2$ and $R_3$ are independently selected from the group consisting of: hydrogen hydroxy and halogen;

n is an integer between 0 and 4;

X is selected from the group consisting of: NH, O and S;

R is:

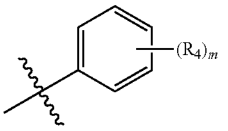

wherein each $R_4$ is independently selected from the group consisting of: halogen, hydroxy, methoxy and amino; and m is an integer between 0 and 4, with the provisio that at least one $R_1$, $R_2$ and $R_3$ is other than hydrogen.

In a second aspect, the present invention provides a pharmaceutical composition comprising a compound of formula (I) according to the first aspect together with a pharmaceutically acceptable carrier, diluent or excipient.

In a third aspect the present invention provides a method for the treatment of a disease or condition associated with $P2X_7R$ in a subject in need thereof, the method comprising administration to the subject of a therapeutically effective amount of a compound of formula (I) according to the first aspect, or a composition of the second aspect.

The disease or condition may be associated with upregulation or increased expression of $P2X_7R$.

The disease or condition may be associated with activation of the $P2X_7R$.

The disease or condition may be an inflammatory disease or condition. In one embodiment, the disease or condition is a neuroinflammatory disease or a neurodegenerative disease.

The disease or condition may be a disease of the central nervous system.

In some embodiments the disease or condition may be one or more of: pain, rheumatoid arthritis, osteoarthritis, sepsis, psoriasis, allergic dermatitis, asthma, chronic obstructive pulmonary disease, airways hyper-responsiveness, septic shock, epilepsy, glomerulonephritis, irritable bowel syndrome, inflammatory bowel disease, Crohn's disease, ulcerative colitis, coronary artery disease, cardiovascular disease, acute coronary syndrome, myocarditis, pericarditis, atherosclerosis, myocardial ischaemia, reperfusion injury, cancer, myoblastic leukaemia, diabetes, Alzheimer's disease, Parkinson's disease, multiple sclerosis, Huntington's disease, glaucoma, multiple sclerosis, amyotrophic lateral sclerosis, depression, age-related macular degeneration, uveitis, neuropathic pain, depression, bipolar affective disorders, anxiety, meningitis, traumatic brain injury, acute spinal cord injury, osteoporosis, burn injury, ischemic heart disease, myocardial infarction, stroke and varicose veins.

In one embodiment the disease or condition is coronary artery disease, cardiovascular disease or atherosclerosis.

In another embodiment the disease or condition is coronary artery disease.

In still a further embodiment the disease or condition is acute coronary syndrome, coronary artery disease, myocarditis, pericarditis, myocardial ischaemia and reperfusion injury.

In a fourth aspect the present invention provides a method for modulating $P2X_7R$ activity in a subject in need thereof, the method comprising administration to the subject of an effective amount of a compound of formula (I) according to the first aspect, or a composition of the second aspect.

Modulating $P2X_7R$ activity may involve inhibiting $P2X_7R$ activity.

In a fifth aspect the present invention provides use of a compound of formula (I) according to the first aspect in the manufacture of a medicament for the treatment of a disease or condition associated with $P2X_7R$.

The disease or condition may be associated with upregulation or increased expression of $P2X_7R$.

The disease or condition may be associated with activation of the $P2X_7R$.

In a sixth aspect the present invention provides use of a compound of formula (I) according to the first aspect in the manufacture of a medicament for modulating $P2X_7R$ activity in a subject.

Modulating P2X7R activity may involve inhibiting P2X7R activity.

Definitions

The following are some definitions that may be helpful in understanding the description of the present invention. These are intended as general definitions and should in no way limit the scope of the present invention to those terms alone, but are put forth for a better understanding of the following description.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

The terms "a" and "an" are used herein to refer to one or to more than one (i.e. to at least one) of the grammatical object of the article. By way of example, "an element" means one element or more than one element.

In the context of this specification, the terms "halo" and "halogen" are synonomous and refer to fluoro, chloro, bromo and iodo.

In the context of this specification, the term "tautomer" refers to structural isomers of different energies which are interconvertible via a low energy barrier.

In the context of this specification, the term "prodrug" means a compound which is able to be converted in vivo by metabolic means (e.g. by hydrolysis, reduction or oxidation) to a compound of the formula (I).

In the context of this specification, the term "cancer" refers to a physiological condition characterised by unregulated cell growth.

In the context of this specification, the term "effective amount" includes a non-toxic but sufficient amount of an active compound to provide the stated/desired effect. Those skilled in the art will appreciate that the exact amount of a compound required will vary based on a number of factors and thus it is not possible to specify an exact "effective amount". However, for any given case an appropriate "effective amount" may be determined by one of ordinary skill in the art.

In the context of this specification, the term "therapeutically effective amount" includes a non-toxic but sufficient amount of an active compound to provide the desired therapeutic effect. Those skilled in the art will appreciate that the exact amount of a compound required will vary based on a number of factors and thus it is not possible to specify an exact "therapeutically effective amount". However, for any given case an appropriate "therapeutically effective amount" may be determined by one of ordinary skill in the art.

In the context of this specification, the terms "treating" and "treatment" refer to any and all uses, which remedy the stated disease or symptoms thereof, hinder, retard or otherwise reverse the progression of the disease or other undesirable symptoms in any way whatsoever. Thus, the terms "treating" and "treatment" are to be considered in their broadest context. For example, treatment does not necessarily imply that a subject is treated until total recovery.

In the context of this specification the term "associated with" when used in the context of a disease or condition "associated with" the $P2X_7R$ means that the disease or condition, or a symptom thereof, may result from, be characterized by, or otherwise related to $P2X_7R$. Thus, the association between the disease or condition and $P2X_7R$ activity may be direct or indirect and may be temporally separated.

In the context of this specification, the term "subject" includes human and also non-human animals. As such, in addition to being useful in the treatment of diseases and conditions in humans, the compounds of the present invention also find use in the treatment of diseases in non-human animals, for example mammals such as companion animals and farm animals. Non-limiting examples of companion animals and farm animals include dogs, cats, horses, cows, sheep and pigs. Preferably, the subject is a human.

In the context of this specification the term "administering" and variations of that term including "administer" and "administration", includes contacting, applying, delivering or providing a compound or composition of the invention to an organism by any appropriate means.

DETAILED DESCRIPTION OF THE INVENTION

Figure 1:
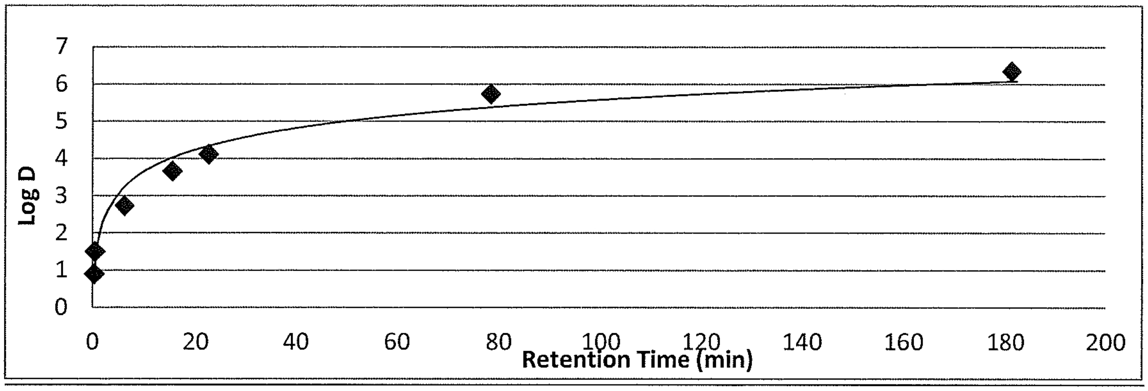
FIG. 1: Calibration curve of standards with known log $D_{7.4}$ values against their HPLC retention times.
Figure 2:
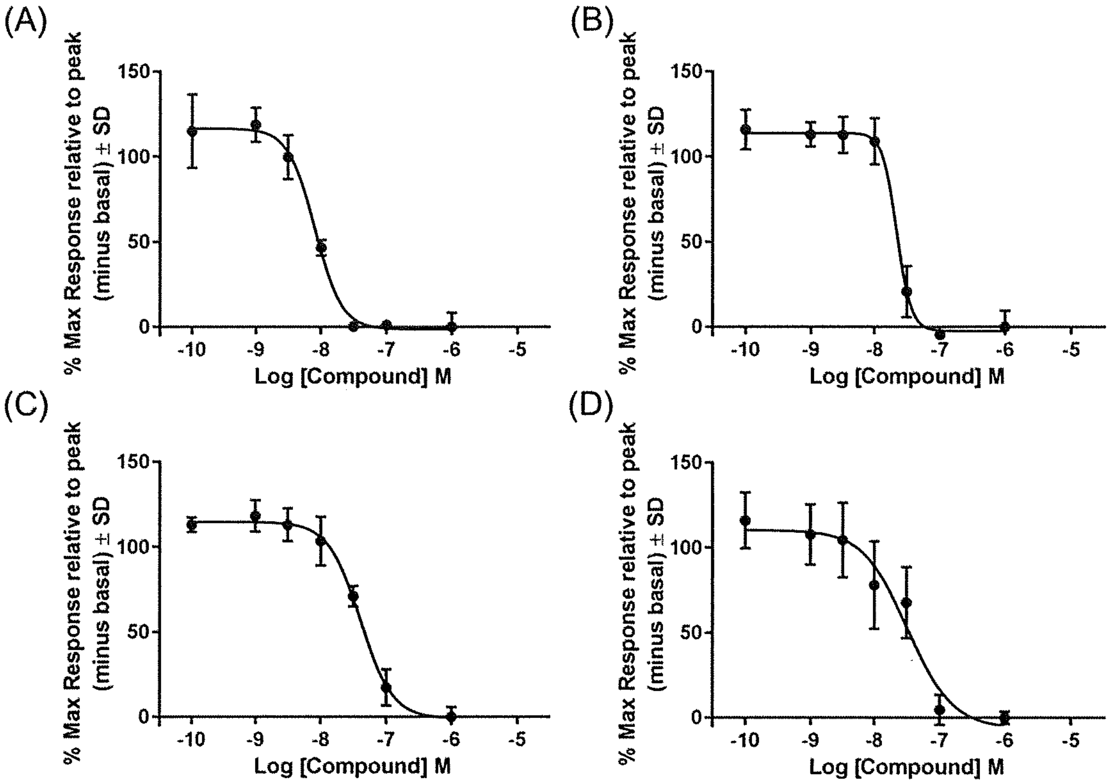
FIG. 2: Inhibition of human $P2X_7R$ pore formation by A) Compound 31, B) Compound 3, C) Compound 2, and D) Compound 1 using a functional dye uptake assay in THP-1 cells. Pore formation was assessed by a BzATP-induced uptake of YO-PRO®-1.

In one aspect the present invention provides a compound of the general formula (I):

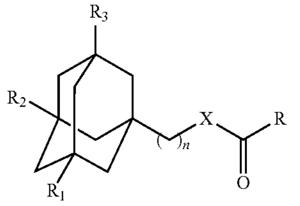

(I)

or a pharmaceutically acceptable salt, hydrate, derivative, solvate, tautomer or prodrug thereof, wherein:

$R_1$, $R_2$ and $R_3$ are independently selected from the group consisting of: hydrogen hydroxy and halogen;

n is an integer between 0 and 4;

X is selected from the group consisting of: NH, O and S;

R is:

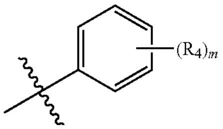

wherein each $R_4$ is independently selected from the group consisting of: halogen, hydroxy, methoxy and amino; and m is an integer between 0 and 4, with the provisio that at least one $R_1$, $R_2$ and $R_3$ is other than hydrogen.

In one embodiment $R_1$, $R_2$ and $R_3$ are independently selected from hydrogen and halogen.

In another embodiment $R_1$, $R_2$ and $R_3$ are independently selected from hydrogen, F, Br and Cl.

In a further embodiment $R_1$, $R_2$ and $R_3$ are independently selected from hydrogen and F.

In still a further embodiment $R_1$, $R_2$ and $R_3$ are all F.

In one embodiment n is an integer between 1 and 4.

In another embodiment n is an integer between 1 and 3.

In a further embodiment n is 1 or 2.

In yet another embodiment n is 1.

In one embodiment, X is NH.

In another embodiment each $R_4$ is independently selected from the group consisting of: halogen, hydroxy and methoxy.

In a further embodiment each $R_4$ is independently selected from the group consisting of: halogen and methoxy.

In yet another embodiment each $R_4$ is independently selected from the group consisting of: Cl, Br and methoxy.

In still a further embodiment each $R_4$ is independently selected from the group consisting of: Cl and methoxy.

In one embodiment m is an integer between 1 and 4.

In another embodiment m is an integer between 1 and 3.

In a further embodiment m is 1 or 2.

In still another embodiment m is 2.

In one embodiment m is 2, one $R_4$ is methoxy and the other $R_4$ is Cl.

In some embodiments R is selected from the group consisting of:

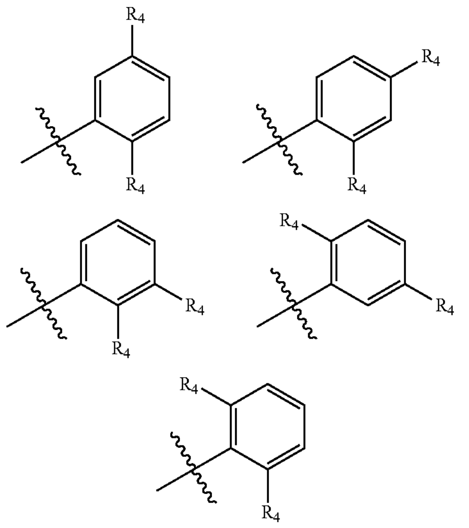

In another embodiment R is selected from the group consisting of:

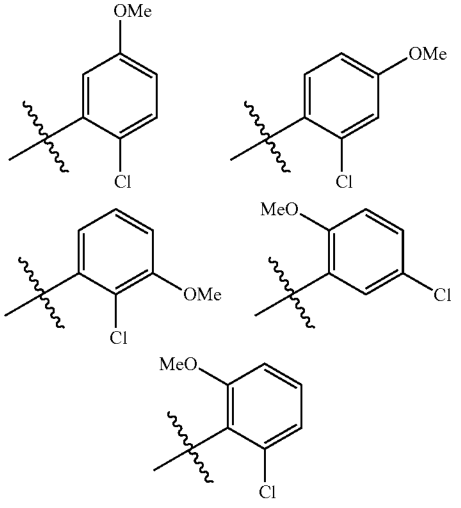

In further embodiments R is selected from the group consisting of:

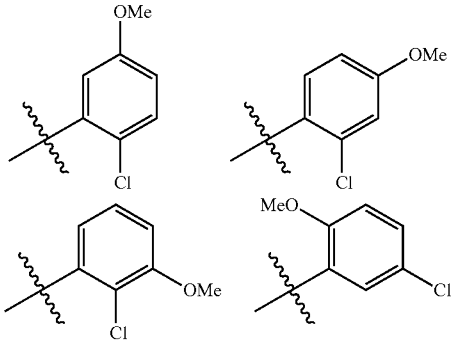

Exemplary compounds of the formula (I) include:
1
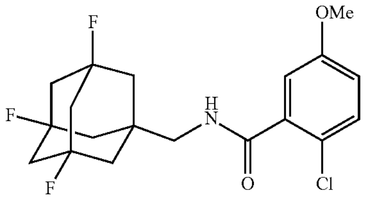
2
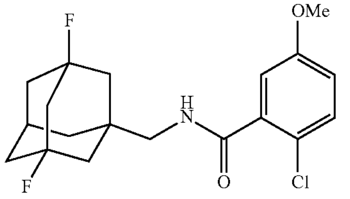
3
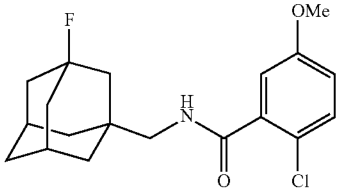
4
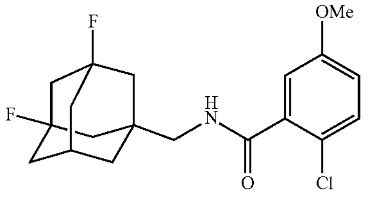
5
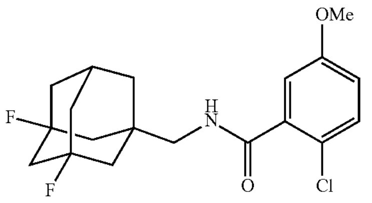
6
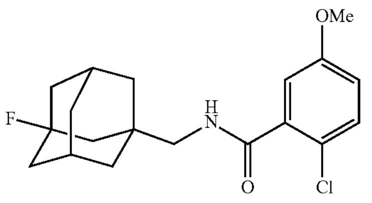
7
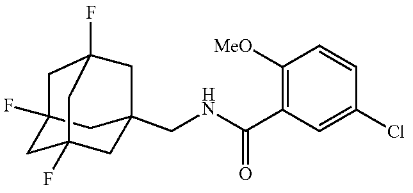
-continued
8
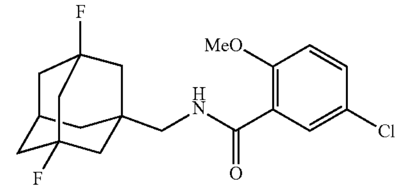
9
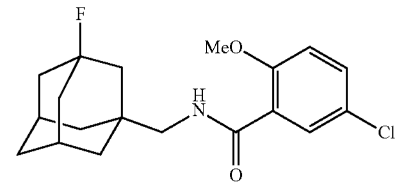
10
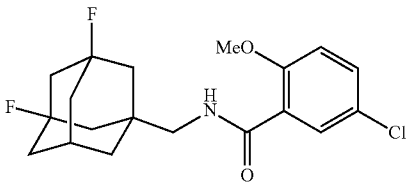
11
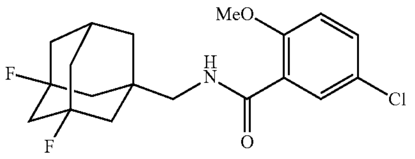
12
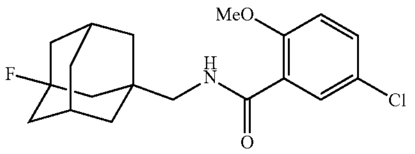
13
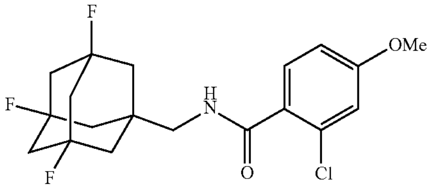
14
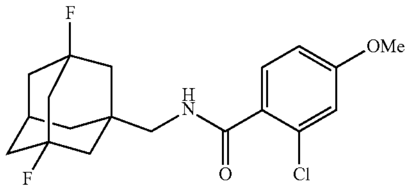
15
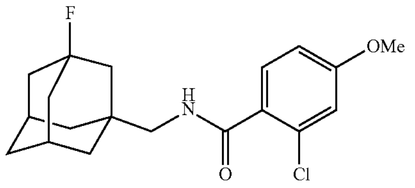

-continued

16

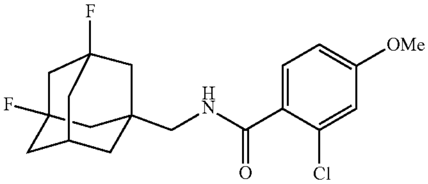

17

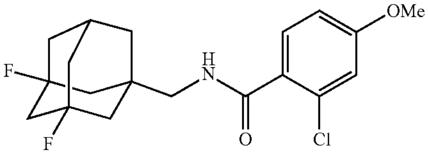

18

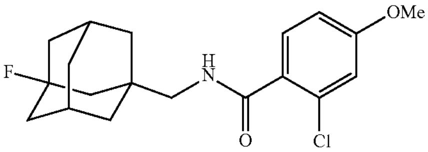

19

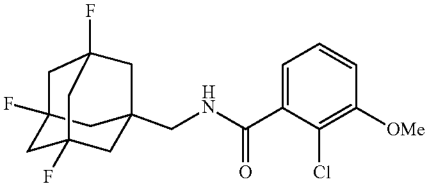

20

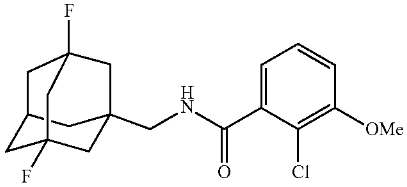

21

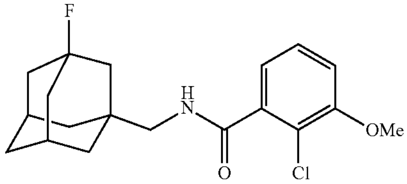

22

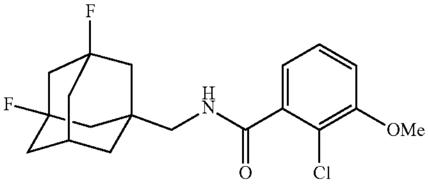

23

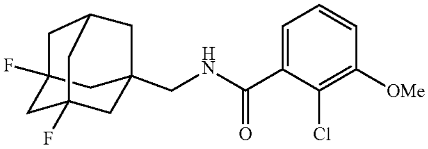

24

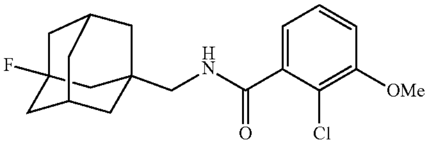

-continued

25

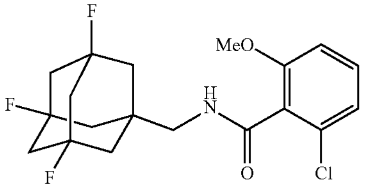

26

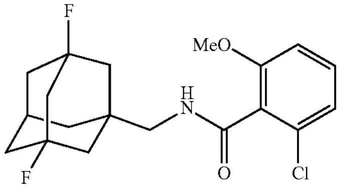

27

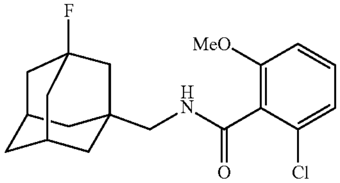

28

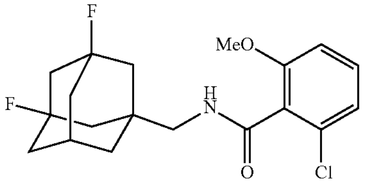

29

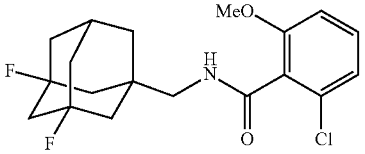

30

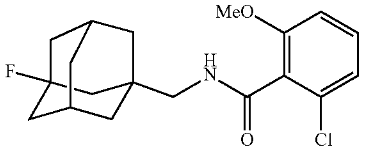

In one embodiment the compound of formula (I) is one or more of compounds 1, 2 and 3. In another embodiment the compound of formula (I) is compound 1.

Compounds of the formula (I) are also taken to include hydrates and solvates. Solvates are complexes formed by association of molecules of a solvent with a compound of the formula (I). Examples of solvents that are capable of forming solvates include, but are not limited to water, isopropanol, ethanol, methanol, DMSO, ethyl acetate and ethanolamine.

In the case of compounds of the formula (I) that are solids, it will be understood by those skilled in the art that such compounds may exist in different crystalline or polymorphic forms, all of which are intended to be within the scope of the present invention.

The compounds of formula (I) may be in the form of pharmaceutically acceptable salts. Such salts are well known to those skilled in the art. S. M. Berge et al. describe pharmaceutically acceptable salts in detail in *J. Pharmaceutical Sciences,* 1977, 66:1-19. Pharmaceutically acceptable salts can be prepared in situ during the final isolation and purification of compounds of the formula (I) or separately by, for example, reacting the free base compound with a suitable organic acid. Suitable pharmaceutically acceptable acid addition salts of the compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, ascorbic, glucoronic, fumaric, maleic, pyruvic, alkyl sulfonic, arylsulfonic, aspartic, glutamic, benzoic, anthranilic, mesylic, salicylic, p-hydroxybenzoic, phenylacetic, mandelic, ambonic, pamoic, pantothenic, sulfanilic, cyclohexylaminosulfonic, stearic, algenic, β-hydroxybutyric, galactaric, and galacturonic acids. Suitable pharmaceutically acceptable base addition salts of the compounds of the present invention include metallic salts made from lithium, sodium, potassium, magnesium, calcium, aluminium, and zinc, and organic salts made from organic bases such as choline, diethanolamine and morpholine. Alternatively, organic salts made from N,N'-dibenzylethylenediamine, chloroprocaine, choline, diethanolamine, ethylenediamine, meglumine (N-methylglucamine), procaine, ammonium salts, quaternary salts such as tetramethylammonium salt, amino acid addition salts such as salts with glycine and arginine.

The compounds of formula (I) may also exist in different tautomeric forms, and all such forms are within the scope of the invention. The compounds of formula (I) also extend to include all derivatives with physiologically cleavable leaving groups that can be cleaved in vivo to provide the compounds of the formula (I).

The present invention also includes isotopically labelled compounds of formula (I). Such compounds are identical to the compounds of formula (I) except that one or more atoms have each been replaced by an atom having the same atomic number but a different atomic mass.

Representative compounds of the formula (I) may be synthesised according to the following general schemes:

Scheme 1

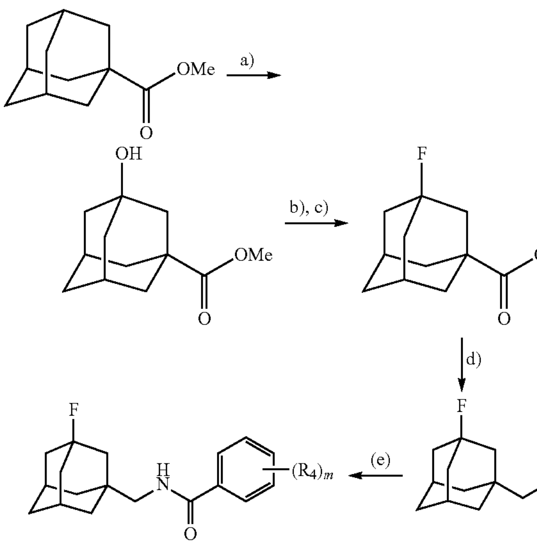

-continued (a) $HNO_3$, $H_2SO_4$, then $EtOAc/H_2O$, $(NH_2)_2CO$;
(b) Deoxyfluor, $CHCl_3$;
(c) NaOH, MeOH, Δ;
(d)(i) CDI, THF, then $NH_4OH$(aq), (ii) $LiAlH_4$, THF;
(e) suitably functionalised benzoic acid, PyBOP, DIPEA, $CH_2Cl_2$.

Scheme 2

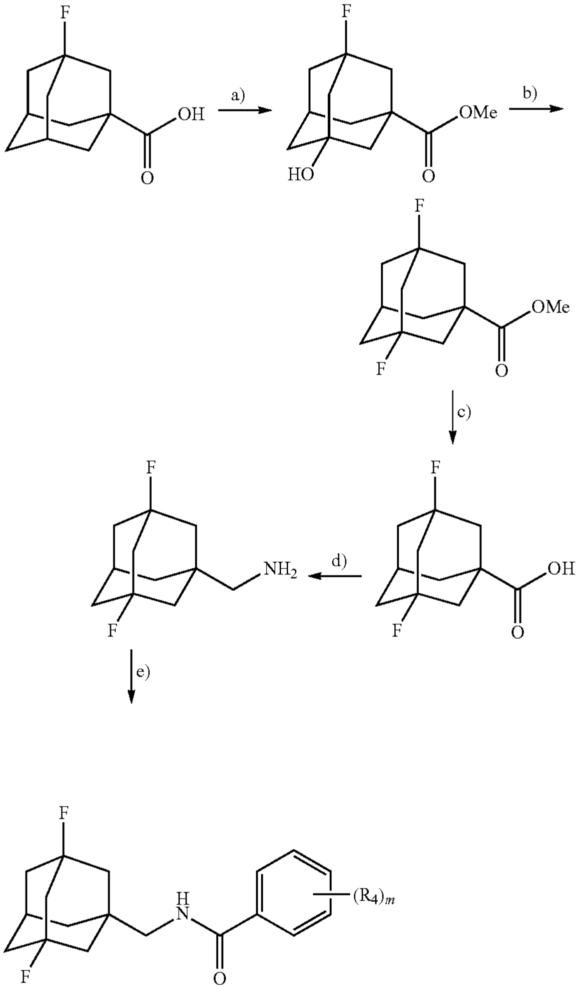

(a)(i) $KMnO_4$, KOH, $H_2O$ then HCl; (ii) $H_2SO_4$, MeOH;
(b) Deoxyfluor, $CHCl_3$;
(c) NaOH, MeOH, Δ;
(d)(i) CDI, THF, then $NH_4OH$(aq), (ii) $LiAlH_4$, THF;
(e) suitably functionalised benzoic acid, PyBOP, DIPEA, $CH_2Cl_2$.

Scheme 3

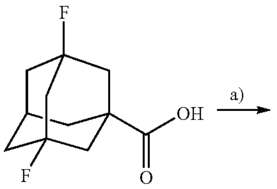

-continued

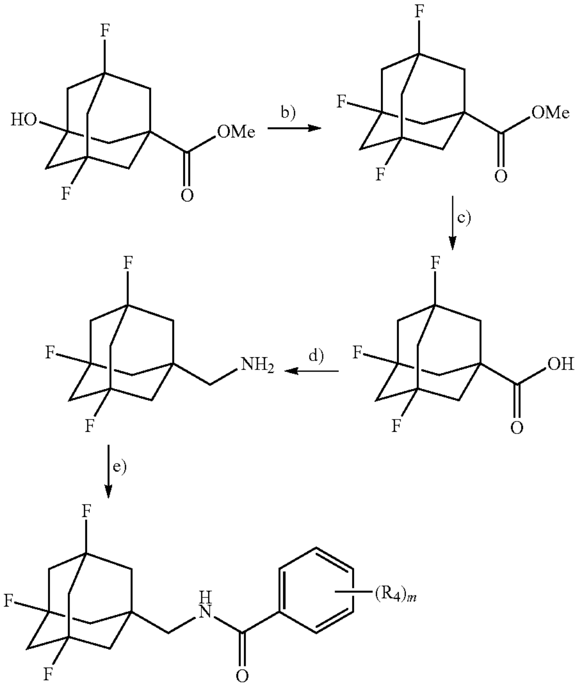

(a)(i) $KMnO_4$, KOH, $H_2O$ then HCl; (ii) $H_2SO_4$, MeOH;
(b) Deoxyfluor, $CHCl_3$;
(c) NaOH, MeOH, Δ;
(d)(i) CDI, THF, then $NH_4OH$(aq), (ii) $LiAlH_4$, THF;
(e) suitably functionalised benzoic acid, PyBOP, DIPEA, $CH_2Cl_2$.

The present inventors have discovered that compounds of the formula (I) are potent $P2X_7R$ antagonists. The compounds may therefore find use in the treatment of diseases or conditions associated with $P2X_7R$, such as diseases or conditions associated with upregulation or increased expression of $P2X_7R$ and/or diseases or conditions associated with activation of the $P2X_7R$.

The disease or condition may be, for example, pain, a neurodegenerative disease, a neuroinflammatory disease, a bone or joint disease, an obstructive disease of the airways, a cardiovascular disease, an eye disease, a skin disease, an abdominal or gastrointestinal tract disease, a genitourinary disease, cancer, an auto-immune disease, an allergic disorder, or other disorder with an inflammatory or immunological component.

In some embodiments the disease or condition is one or any combination of the following: pain, rheumatoid arthritis, osteoarthritis, sepsis, psoriasis, allergic dermatitis, asthma, chronic obstructive pulmonary disease, airways hyper-responsiveness, septic shock, epilepsy, glomerulonephritis, irritable bowel syndrome, inflammatory bowel disease, Crohn's disease, ulcerative colitis, coronary artery disease, cardiovascular disease, acute coronary syndrome, myocarditis, pericarditis, atherosclerosis, myocardial ischaemia, reperfusion injury, cancer, myoblastic leukaemia, diabetes, Alzheimer's disease, Parkinson's disease, multiple sclerosis, Huntington's disease, glaucoma, multiple sclerosis, amyotrophic lateral sclerosis, depression, age-related macular degeneration, uveitis, neuropathic pain, depression, bipolar affective disorders, anxiety, meningitis, traumatic brain injury, acute spinal cord injury, osteoporosis, burn injury, ischemic heart disease, myocardial infarction, stroke and varicose veins. Those skilled in the art will appreciate that the compounds of formula (I) may also find use in the treatment of other diseases and conditions in which inhibition of $P2X_7R$ activity provides a therapeutic benefit.

Compounds and pharmaceutical compositions of the present invention may be administered via any route that delivers an effective amount of the compounds to the tissue or site to be treated. In general, the compounds and compositions may be administered by the parenteral (for example intravenous, intraspinal, subcutaneous or intramuscular), oral, inhalation, or topical route. Administration may be systemic, regional or local.

The particular route of administration to be used in any given circumstance will depend on a number of factors, including the nature of the disease or condition to be treated, the severity and extent of the disease or condition, the required dosage of the particular compound to be delivered and the potential side-effects of the compound.

In general, suitable compositions may be prepared according to methods that are known to those of ordinary skill in the art and may include pharmaceutically acceptable carriers, diluents and/or excipients. The carriers, diluents and excipients must be "acceptable" in terms of being compatible with the other ingredients of the composition, and not deleterious to the recipient thereof.

Examples of pharmaceutically acceptable carriers or diluents are demineralised or distilled water; saline solution; vegetable-based oils such as peanut oil, safflower oil, olive oil, cottonseed oil, maize oil or coconut oil; silicone oils, including polysiloxanes, such as methyl polysiloxane, phenyl polysiloxane and methylphenyl polysiloxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; Cremaphor; cyclodextrins; lower alcohols, for example ethanol or i-propanol; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia and petroleum jelly. Typically, the carrier or carriers will form from 10% to 99.9% by weight of the compositions.

Pharmaceutical compositions of the invention may be in a form suitable for administration by injection, in the form of a formulation suitable for oral ingestion (such as capsules, tablets, caplets and elixirs for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include cyclodextrins (for example Captisol®) Cremaphor, Ringer's solution, isotonic saline, phosphate buffered saline, ethanol and 1,2-propylene glycol. To aid injection and delivery, the compounds may also be added to PEG and non-PEGylated liposomes or micelles with specific targeting tags attached to PEG moieties, such as the RGD peptide or glutathione, for aiding passage across the blood brain barrier.

Some examples of suitable carriers, diluents, excipients and adjuvants for oral use include cyclodextrins, Cremaphor, peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition, these oral formulations may contain suitable flavouring and colourings agents. When used in capsule form the capsules may be coated with compounds such as glyceryl monostearate or glyceryl distearate that delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharin. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time-delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethylcellulose, polyvinylpyrrolidone, sodium alginate or acetyl alcohol. Suitable dispersing agents include lecithin, polyoxyethylene esters of fatty acids, such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further comprise one or more emulsifying agents. Suitable emulsifying agents include dispersing agents as exemplified above or natural gums such as guar gum, gum acacia or gum tragacanth. A further suitable emulsifying agent for use in oral or parenteral formulations, which may also function as a solubilizer, is Kolliphor® HS 15.

Methods for preparing parenterally administrable compositions are apparent to those skilled in the art, and are described in more detail in, for example, Remington's Pharmaceutical Science, 15th ed., Mack Publishing Company, Easton, PA, hereby incorporated by reference herein.

Topical formulations may comprise an active ingredient together with one or more acceptable carriers, and optionally any other therapeutic ingredients. Formulations suitable for topical administration include liquid or semi-liquid preparations suitable for penetration through the skin to the site where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisation may be achieved by autoclaving or maintaining at 90° C. to 100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisiteriser such as glycerol, or oil such as olive oil.

Creams, ointments or pastes according to the present invention are semi-solid formulations of the active ingredient for external application. They may be made by mixing the active ingredient in finely divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol, such as propylene glycol or macrogols.

The composition may incorporate any suitable surfactant such as an anionic, cationic or non-ionic surfactant, such as sorbitan esters or polyoxyethylene derivatives thereof. Suspending agents such as natural gums, cellulose derivatives or inoraganic materials such as silicaceous silicas, and other ingredients such as lanolin, may also be included.

In some embodiments the compositions are administered in the form of suppositories suitable for rectal administration of the compounds. These compositions are prepared by mixing the compound with a suitable non-irritating excipient which is solid at ordinary temperatures but liquid at the rectal temperature and will therefore melt in the rectum to release the zeolite or zeolite-like material. Such materials include cocoa butter, glycerinated gelatin, hydrogenated vegetable oils, mixtures of polyethylene glycols of various molecular weights and fatty acid esters of polyethylene glycol.

The compositions may also be administered or delivered to target cells in the form of liposomes. Liposomes are generally derived from phospholipids or other lipid substances and are formed by mono- or multi-lamellar hydrated liquid crystals that are dispersed in an aqueous medium. Specific examples of liposomes used in administering or delivering a composition to target cells are synthetic cholesterol (Sigma), the phospholipid 1,2-distearoyl-sn-glycero-3-phosphocholine (DSPC); Avanti Polar Lipids), the PEG lipid 3-N-[(-methoxy poly(ethylene glycol)2000)carbamoyl]-1,2-dimyrestyloxy-propylamine (PEG-cDMA), and the cationic lipid 1,2-di-o-octadecenyl-3-(N,N-dimethyl)aminopropane (DODMA) or 1,2-dilinoleyloxy-3-(N,N-dimethyl)aminopropane (DLinDMA) in the molar ratios 55:20:10:15 or 48:20:2:30, respectively, PEG-cDMA, DODMA and DLinDMA. Any non-toxic, physiologically acceptable and metabolisable lipid capable of forming liposomes can be used. The compositions in liposome form may contain stablisers, preservatives, excipients and the like. The preferred lipids are the phospholipids and the phosphatidyl cholines (lecithins), both natural and synthetic. Methods to form liposomes are known in the art, and in relation to this, specific reference is made to: Prescott, Ed., *Methods in Cell Biology*, Volume XIV, Academic Press, New York, N.Y. (1976), p. 33 et seq., the contents of which is incorporated herein by reference.

The compositions may also be administered in the form of microparticles or nanoparticles. Biodegradable microparticles formed from polyactide (PLA), polylactide-co-glycolide (PLGA), and epsilon-caprolactone (ε-caprlactone) have been extensively used as drug carriers to increase plasma half life and thereby prolong efficacy (R. Kumar, M., 2000, *J. Pharm. Pharmaceut. Sci.* 3(2) 234-258). Microparticles have been formulated for the delivery of a range of drug candidates including vaccines, antibiotics, and DNA. Moreover, these formulations have been developed for various delivery routes including parenteral subcutaneous injection, intravenous injection and inhalation.

The compositions may incorporate a controlled release matrix that is composed of sucrose acetate isobutyrate (SAIB) and an organic solvent or organic solvents mixture. Polymer additives may be added to the vehicle as a release modifier to further increase the viscosity and slow down the release rate. SAIB is a well known food additive. It is a very hydrophobic, fully esterified sucrose derivative, at a nominal ratio of six isobutyrate to two acetate groups. As a mixed ester, SAIB does not crystallise but exists as a clear viscous liquid. Mixing SAIB with a pharmaceutically acceptable organic solvent, such as ethanol or benzyl alcohol decreases the viscosity of the mixture sufficiently to allow for injection. An active pharmaceutical ingredient may be added to the SAIB delivery vehicle to form SAIB solution or suspension formulations. When the formulation is injected subcutaneously, the solvent differs from the matrix allowing the SAIB-drug or SAIB-drug-polymer mixtures to set up as an in situ forming depot.

For the purposes of the present invention compounds and compositions may be administered to subjects either therapeutically or preventively. In a therapeutic application compositions are administered to a patient already suffering from a disease or condition in an amount sufficient to cure or at least partially arrest the disease or condition and its complications. The composition should provide a quantity of the compound or agent sufficient to effectively treat the subject.

The therapeutically effective amount for any particular subject will depend upon a variety of factors including: the disease or condition being treated and the severity thereof; the activity of the compound administered; the composition in which the compound is present; the age, body weight, general health, sex and diet of the subject; the time of administration; the route of administration; the rate of sequestration of the compound; the duration of the treatment; drugs used in combination or coincidental with the compound, together with other related factors well known in medicine. One skilled in the art would be able, by routine experimentation, to determine an effective, non-toxic amount of a compound that would be required to treat or prevent a particular disease or condition.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 $mg/m^2$. Generally, an effective dosage is expected to be in the range of about 25 to about 500 $mg/m^2$, preferably about 25 to about 350 $mg/m^2$, more preferably about 25 to about 300 $mg/m^2$, still more preferably about 25 to about 250 $mg/m^2$, even more preferably about 50 to about 250 $mg/m^2$, and still even more preferably about 75 to about 150 $mg/m^2$.

Typically, in therapeutic applications, the treatment would be for the duration of the disease or condition.

Further, it will be apparent to one of ordinary skill in the art that the optimal quantity and spacing of individual dosages will be determined by the nature and extent of the disease or condition being treated, the form, route and site of administration, and the nature of the particular individual being treated. Also, such optimum conditions can be determined by conventional techniques.

The present invention is further described below by reference to the following non-limiting examples.

EXAMPLES

Example 1—General Synthetic Procedures

General Procedure A: Oxidation of Adamantanes

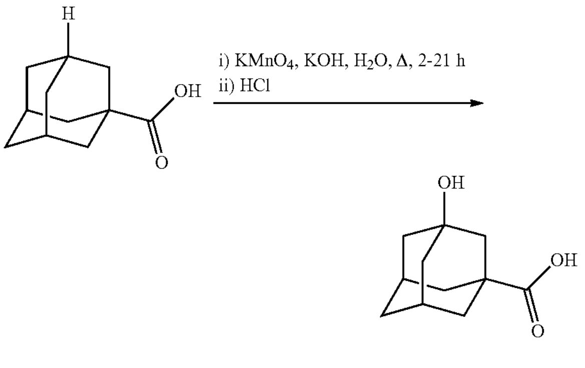

Potassium hydroxide (1.0 mmol) and potassium permanganate (1.1 mmol) were dissolved in water (2 mL) and heated to 50-60° C. with stirring. After 30 min, a high stirring speed was used whilst the adamantane-carboxylic acid (1.0 mmol) was added portionwise in a manner that allowed each portion to stir into solution before the next portion was added. The stirring speed was reduced and the reaction heated to reflux until the intense purple coloration turned brown. The reaction was cooled to room temperature and then over ice. Concentrated hydrochloric acid (0.5 mL)

is added dropwise with stirring which results in a white precipitate and effervescence. Sodium bisulfite is added portionwise until the black solution turns white. The product and unconsumed starting material is extracted into 10% methanol in ethyl acetate solution (3×5 mL), dried over magnesium sulfate and then the solvent removed by rotary evaporation. Purification can be achieved by flash chromatography (1:1 ethyl acetate:hexane) however, due to solubility issues, it is more practical to purify the product from recovered starting material after the Fischer esterification.

General Procedure B: Fischer Esterification of Adamantane Carboxylic Acids

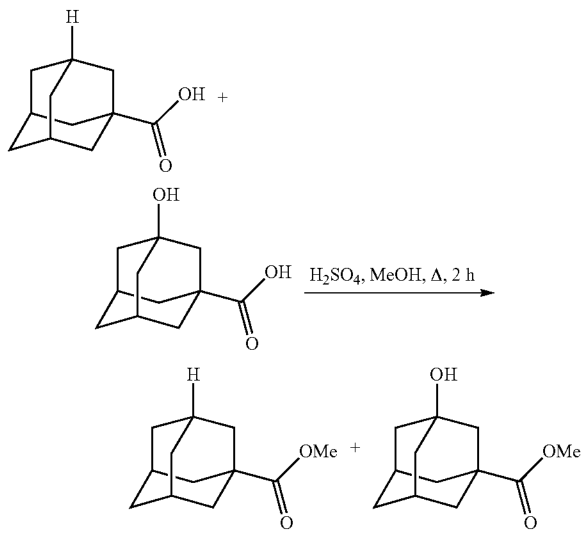

Concentrated sulfuric acid (0.3 mL) was added to adamantane carboxylic acid (a 1 g mixture of the adamantane carboxylic acid and hydroxyadamantane carboxylic acid was used following the permanganate oxidation step) dissolved in methanol (10 mL). The solution was refluxed until reaction was deemed complete (2-3 h) by TLC (1:1 ethyl acetate:hexane). The solution was cooled to room temperature and the methanol was removed by rotary evaporation. The residue was dissolved in ethyl acetate (6 mL) and washed with sodium hydroxide (3 M, 3 mL). The aqueous layer was washed with additional ethyl acetate (2×6 mL) and the organic layers were combined, dried over magnesium sulfate and evaporated to dryness by rotary evaporation. Purification was achieved by flash chromatography (1:3 ethyl acetate:hexane to resolve the methyl adamantane-carboxylate then increase to 100% ethyl acetate to elute the methyl hydroxyadamantane-carboxylate).

General Procedure C: Deoxyfluorination of Adamantanes

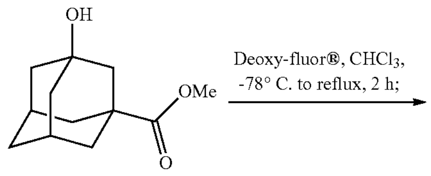

-continued

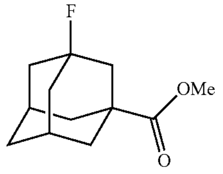

Deoxo-Fluor® (1.1 mol) in anhydrous chloroform (2 mL) was cooled to −78° C. under a nitrogen atmosphere. Methyl 3-hydroxyadamantane-1-carboxylate (1.0 mmol) dissolved in anhydrous chloroform (3 mL) was added dropwise with stirring and the solution was allowed to warm to room temperature (30 min) and then heated at reflux for 1-2 h. The reaction was cooled to room temperature and then poured into saturated sodium bicarbonate (25 mL). Dichloromethane (15 mL) was added and after the effervescence ceased, the organic layer was collected and the aqueous layer was extracted with dichloromethane (2×15 mL). The organic layers were combined, dried ($MgSO_4$), filtered and evaporated to dryness by rotary evaporation. Purification was achieved by flash chromatography (1:9 ethyl acetate: hexane).

General Procedure D: Saponification of Adamantane-Esters

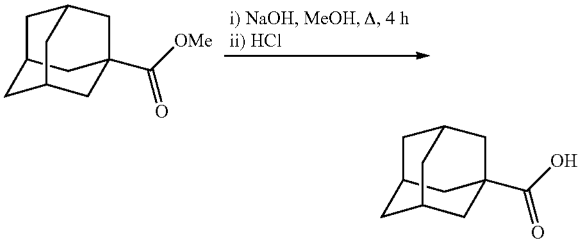

Aqueous sodium hydroxide (1 M, 2 mL) was added to methyl adamantanecarboxylate (1.0 mmol) dissolved in methanol (2 mL) and the solution was refluxed until reaction was deemed complete (2-3 h) by TLC (1:9 ethyl acetate: hexane). Methanol was removed by rotary evaporation and then water (5 mL) and diethyl ether (2 mL) were added. The aqueous layer was collected and acidified to pH 1. The resulting white precipitate was extracted into ethyl acetate (2×10 mL), dried ($MgSO_4$), filtered and evaporated to dryness by rotary evaporation. The product was used in further steps without further purification.

General Procedure E: Amidation of Adamantane-Carboxylic Acids

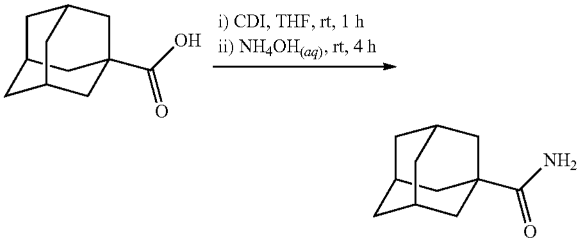

Adamantanecarboxylic acid (1.0 mmol) and 1,1'-carbonyldiimidazole (1.2 mmol) were stirred for 1 h at room temperature in THF (4 mL) under a $N_2$ atmosphere. The reaction was cooled on ice then aqueous ammonia (28%, 0.5 mL) was added. The reaction was stirred for 4 h, allowing the solution to warm to room temperature. The solvent was removed by rotary evaporation and the residue dissolved in dichloromethane (15 mL) and washed with aqueous sodium hydroxide (1 M, 5 mL), then aqueous hydrochloric acid (1 M, 5 mL) and then water (5 mL). The organic layer was dried ($MgSO_4$), filtered and evaporated to dryness to yield adamantanecarboxamide.

General Procedure F: Reduction of Adamantane-Carboxamides to Adamantanemethylamines

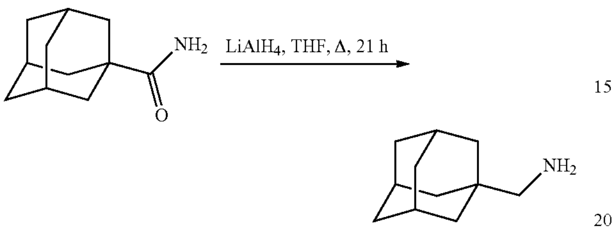

A solution of adamantanecarboxamide (1 mmol) in THF (4 mL) was treated with $LiAlH_4$ (4 mmol) at 0° C. and stirred under a $N_2$ atmosphere whilst warming to room temperature. After 2 h, the reaction was heated at reflux for 16 h and then cooled on ice. Chilled $H_2O$ (150 μL) was added dropwise, with vigorous stirring, and then followed by aqueous sodium hydroxide (15% w/v, 150 μL) and additional water (0.5 mL). The solution was left stirring at room temperature until effervescence had ceased and the grey powder had turned white (30 min). The solution was dried ($MgSO_4$) and then filtered. The precipitate was washed with additional dichloromethane (2×4 mL). The filtrates in each case were combined. Purification was carried out as follows:

When the free base is immediately required: The combined organic extracts were evaporated by rotary evaporation to yield a yellow-orange oil. This oil was purified by flash chromatography (1:19 methanol:dichloromethane +0.1% ammonia).

For long term storage (>1 week), the hydrochloride salt is more stable: The combined organic extracts were washed with NaOH (1 M, 5 mL) and then $H_2O$ (5 mL) and then dried ($MgSO_4$), filtered and evaporated to dryness by rotary evaporation. The resulting filtrate was treated with HCl in dioxane (4 M, 2 mL). The resulting white precipitate was collected by filtration and washed with $Et_2O$ to yield adamantan-1-ylmethylamine hydrochloride.

General Procedure G: Amide Coupling via Acid Chloride

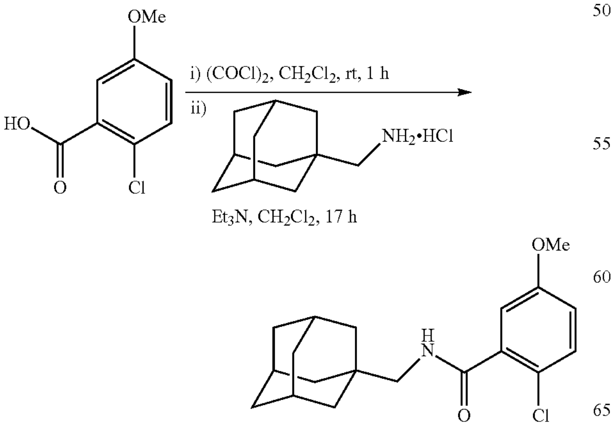

Oxalyl chloride (2.2 mmol) was added to carboxylic acid (1.0 mmol) in tetrahydrofuran or dichloromethane (4 mL). A drop of dimethylformamide was added to the solution which resulted in effervescence and the reaction mixture was left stirring at room temperature under a $N_2$ atmosphere. After 1 h, the solvent was removed by a stream of $N_2$ gas and the acid chloride dried for 0.5 h under a high vacuum (<10 mbar). The acid chloride was dissolved in tetrahydrofuran or dichloromethane (4 mL) and added to adamantan-1-ylmethylamine (free base or HCl salt, 540 mg, 2.68 mmol) with tetrahydrofuran or dichloromethane washings (2 mL). $Et_3N$ (800 μL, 2.0 mmol) was added to the reaction mixture which was then left stirring at room temperature under a $N_2$ atmosphere overnight (18 h). The solvent was removed by rotary evaporation and the residue partitioned between ethyl acetate (30 mL) and aqueous sodium hydroxide (1 M, 15 mL). The organic layer was collected and washed with aqueous hydrochloric acid (1 M, 15 mL) before being dried ($MgSO_4$), filtered and evaporated to dryness. The resulting residue was subjected to flash chromatography (1:3 ethyl acetate:hexane) to yield N-(adamantan-1-ylmethyl)-2-chloro-5-methoxybenzamides General Procedure H: Amide Coupling with PyBOP

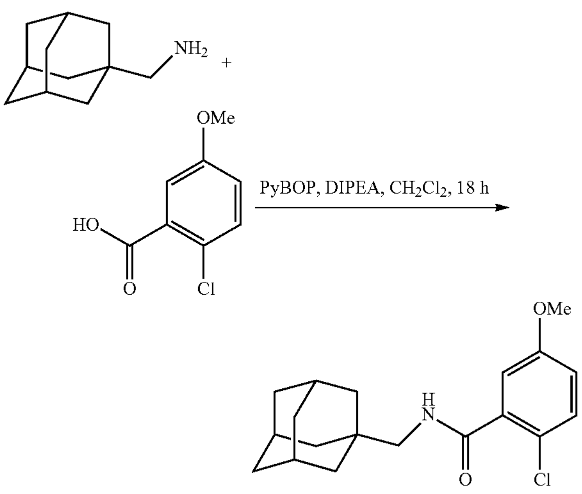

(Benzotriazol-1-yloxy)tripyrrolidinophosphonium hexafluorophosphate (PyBOP, 1.1 mmol) was added to a solution of adamantan-1-ylmethylamine (1.0 mmol), 2-chloro-5-methoxybenzoic acid (1.1 mmol), and diisopropylethylamine (1.75 mmol) dissolved in dichloromethane or tetrahydrofuran (10 mL). The reaction was stirred overnight (18 h) at room temperature under a nitrogen atmosphere. The reaction was then washed with aqueous hydrochloric acid (1 M, 5 mL), then aqeuous sodium hydroxide (1 M, 5 mL), then water (5 mL). The organic layer was dried ($MgSO_4$), filtered and evaporated to dryness by rotary evaporation. The resulting residue was subjected to flash chromatography (1:3 ethyl acetate:hexane) to yield N-(adamantan-1-ylmethyl)-2-chloro-5-methoxybenzamides.

Synthesis of 2-Chloro-5-Methoxybenzoic Acid

2-Chloro-5-hydroxybenzoic acid. 5-Amino-2-chlorobenzoic acid (2.60 g, 15.2 mmol) was suspended in aq. $H_2SO_4$ (1.25% v/v, 240 mL) and cooled below 5° C. with an ice bath. A solution of $NaNO_2$ (1.55 g, 225 mmol) in $H_2O$ (45 mL) was added dropwise to maintain a reaction temperature below 5° C. The reaction was stirred until all solids had dissolved and a clear solution resulted (~1 hr). The reaction was poured into hot $H_2O$ (450 mL, 65° C.) and decolorizing charcoal (2 g) was added. The mixture was refluxed for 0.5 h, then cooled to room temperature and filtered. The filtrate was extracted with EtOAc (3×300 mL) and combined and dried over anhyd. $Na_2SO_4$. The solvent was removed by rotary evaporation to give crude 2-chloro-5-hydroxybenzoic acid (1.88 g, 71.5%) as a light brown solid. M.P. 174-177° C. (lit. M.P. 186-189° C.); IR (ZnSe): 3302 (broad, O—H), 1693, 1656, 1569, 1432, 1212, 660 $cm^{-1}$; $^1H$ NMR (300 MHz, $d_6$-DMSO): δ 13.23 (1H, s, broad, $CO_2\underline{H}$), 9.95 (1H, s, broad, ArO$\underline{H}$), 7.29 (1H, d, $J_{H3-H4}$ 8.7, H3), 7.15 (1H, d, $^4J_{H4-H6}$3.0, H6), 6.90 (1H, dd, $^3J_{H3-H4}$8.7, $^4J_{H4-H6}$3.0, H4); $^{13}C$ NMR (75 MHz, $d_6$-DMSO): δ 166.6 (C7), 156.1 (C5), 132.0 (C1), 131.5 (C3), 121.0 (C2), 119.6, 117.2; LRMS (−ESI): m/z 343 ($[2M-H]^-$, 100%), 171 ($[M-H]^-$, 37%). The spectroscopic data matched that reported in the literature.

Methyl 2-chloro-5-methoxybenzoate. Iodomethane (3.0 mL, 49 mmol) was added to 2-chloro-5-hydroxybenzoic acid (1.5 g, 8.7 mmol) and $K_2CO_3$ (5.3 g, 39 mmol) in DMF (75 mL). The reaction mixture was heated at 40° C. for 20 h under a $N_2$ atmosphere, then cooled to RT and quenched with $H_2O$ (150 mL). The ester was extracted with $Et_2O$ (3×100 mL) with the organic layers combined and washed with aq. NaOH (0.1 M, 150 mL), then $H_2O$ (2×100 mL), and then dried over anhyd. $MgSO_4$. The solvent was removed in vacuo to yield the brown oil of methyl 2-chloro-2-methoxybenzoate (1.67 g, 95%). IR (ZnSe): 2953 (w, C—H), 2841 (w, C—H), 1731 (s, C═O), 1478 (m), 1433 (m), 1288 (s), 1218 (s, C—O), 1114 (s), 1055 (s), 1025 (s), 816 (m), 777 (m), 642 (m, C—Cl) $cm^{-1}$; $^1H$ NMR (300 MHz, $CDCl_3$): β 7.35-7.28 (2H, m, H5, H8), 6.94 (1H, dd, $^3J_{H5-H6}$ 9.0, $^4J_{H6-H8}$ 3.0, H6), 3.91 (3H, s, H1), 3.80 (3H, s, H9); $^{13}C$ NMR (75 MHz, $CDCl_3$): δ 166.1 (C2), 158.0 (C7), 131.9 (Ar—H), 130.7 (C3), 125.0 (C4), 119.0 (ArH), 116.1 (ArH), 55.8 (C9), 52.5 (C1) ppm.

2-Chloro-5-methoxybenzoic acid. Methyl 2-chloro-5-methoxybezoate (1.62 g, 8.07 mmol) was dissolved in THF (30 mL) and aq. LiOH (1 M, 40 mL) was added. The solution was heated at reflux for 4 h, then stirred overnight (~16 h). The solution was reduced to half by rotary evaporation then aq. HCl (6 M) was added until pH 1. The resulting white precipitate was extracted into $CH_2Cl_2$ (2×150 mL). The organic layers were combined, dried over anhyd. $MgSO_4$ and evaporated to dryness. The resulting brown gum was recrystallized from $H_2O$ (~200-250 mL) resulting in the tan-colored powder of 2-chloro-5-methoxybenzoic acid 27 (1.145 g, 76%). M.P. 178-180° C. (lit. M.P. 178-181° C.); $^1H$ NMR (400 MHz, DMSO-$d_6$): δ 13.48 (1H, s, broad, $CO_2\underline{H}$), 7.43 (1H, d, $J_{H4-H5}$ 8.8, H4), 7.28 (1H, d, $^4J_{H5-H7}$ 2.4, H7), 7.10 (1H, dd, $^3J_{H4-H5}$ 8.8, $^4J_{H5-H7}$ 2.8, H5), 3.78 (3H, s, H8); $^{13}C$ NMR (75 MHz, DMSO-$d_6$): δ 166.7 (C1), 157.8 (C6), 132.4 (C2), 131.6 (C4), 122.7 (C3), 118.5 (C5), 115.5 (C7), 55.7 (C8) ppm. The spectroscopic data matched that reported in the literature.

Example 2—Synthesis of Compound 3

Adamantane-1-carboxylic acid (20.0 g, 0.10 mmol) was esterified using general procedure B to obtain methyl adamantane-1-carboxylate (20.8 g, 97%) as an off-white solid. M.P. 37-39° C. (lit. m.p. 38-39° C.); IR (Di-ATR): 2903 (C—H), 2852 (C—H), 1726 (C═O), 1235 (C—O), 1073 $cm^{-1}$; $^1H$ NMR (500 MHz, $CDCl_3$): δ 3.63 (3H, s, H6), 2.00 (3H, br s, H4), 1.87 (6H, br s, H3), 1.70 (6H, m, H5) ppm; $^{13}C$ NMR (126 MHz, $CDCl_3$): δ 178.3 (C1), 51.6 (C6), 40.8 (C2), 40.8 (C3), 39.0 (C5), 28.1 (C4) ppm; LRMS (+APCI): 195 ($[M+H]^+$, 100).

Methyl 3-hydroxyadamantane-1-carboxylate. Concentrated nitric acid (70%, 1.8 mL) was added dropwise to concentrated sulfuric acid (98%, 26 mL) on ice. Methyl adamantane-1-carboxylate (5.03 g, 25.9 mmol) was added in portions to the acidic solution on ice with vigorous stirring. The ice was removed and the reaction was stirred at room temperature for 2 hours. The reaction mixture was slowly added to an ice-cold solution of ethyl acetate (110 mL), water (120 mL) and urea (3.87 g, 64.4 mmol). The ice bath was removed and the mixture allowed to stir at room temperature for 4 hours. The layers were separated and the water layer was extracted with ethyl acetate (2×50 mL). The combined organic extracts were washed with water (50 mL), aqueous sodium carbonate (10%, 50 mL) until basic, and then brine (50 mL). The organic layer was dried over magnesium sulfate and evaporated to dryness by rotary evaporation to yield crude methyl 3-hydroxyadamantane-1-carboxylate as an oil. Purification by flash chromatography (1:3 ethyl acetate:hexane until SM elutes, then 100% ethyl acetate) yielded pure methyl 3-hydroxyadamantane-1-carboxylate (4.18 g, 76%) as a colorless oil. IR (Di-ATR): 3388 (O—H), 2908 (C—H), 2855 (C—H), 1726 (C═O), 1709, 1454, 1232 (C—O), 1120, 1100, 1029 $cm^{-1}$; $^1H$ NMR (400 MHz, $CDCl_3$): δ 3.63 (3H, s, H9), 2.23 (2H, br s, H6), 1.82 (2H, m, H3), 1.76 (4H, m, H5), 1.67 (4H, m, H7), 1.56 (2H, m, H8) ppm; $^{13}C$ NMR (100 MHz, $CDCl_3$): δ 177.0 (C1), 68.3 (C4), 51.9 (C9), 46.4 (C3), 44.4 (C7), 44.1 (C2), 37.8 (C5), 35.1 (C8), 30.3 (C6) ppm; LRMS (+ESI): 274 (70), 242 (15), 211 ($[M+H]^+$, 100).

Methyl 3-fluoroadamantane-1-carboxylate. Methyl 3-hydroxyadamantane-1-carboxylate (10.2 g, 48.5 mmol) was subjected to deoxyfluorination, using general procedure C, to obtain methyl 3-fluoroadamantane-1-carboxylate (9.27 g, 90%) as a colorless solid. M.P. 30-32° C. (lit. m.p. 34° C.); IR (Di-ATR): 2943 (C—H), 2916 (C—H), 2863 (C—H), 1728 (C═O), 1252, 1226 (C—O), 1095, 1016 (C—F), 924, 873 $cm^{-1}$; $^1H$ NMR (500 MHz, $CDCl_3$): δ 3.67 (3H, s, H9), 2.34 (2H, br s, H6), 2.01 (1H, d, $^3J_{H3-F}$=5.5 Hz, H3), 1.86 (4H, m, H7), 1.79 (4H, m, H5), 1.59 (2H, m, H8) ppm; $^{13}C$ NMR (126 MHz, $CDCl_3$): δ 176.4 (d, $^4J_{C1-F}$=1.3 Hz, C1), 92.3 (d, $^1J_{C4-F}$=183.6 Hz, C4), 52.0 (s, C9), 45.0 (d, $^3J_{C2-F}$=11.3 Hz, C2), 43.9 (d, $^2J_{C3-F}$=20.1 Hz, C3), 42.0 (d, $^2J_{C7-F}$=17.6 Hz, C7), 37.7 (d, $^4J_{C5-F}$=2.5 Hz, C5), 34.9 (d, $^4J_{C8-F}$=1.3 Hz, C8), 31.0 (d, $^3J_{C6-F}$=10.1 Hz, C6) ppm; $^{19}F$ NMR (471 MHz, $CDCl_3$): δ −132.4 (s, C4-F) ppm; LRMS (+APCI): 193 ($[M-F]^+$, 100), 213([M+H]+, 65).

3-Fluoroadamantane-1-carboxylic acid. Methyl 3-fluoroadamantane-1-carboxylate (9.24 g, 43.5 mmol) was saponified using general procedure D, to obtain 3-fluoroadamantane-1-carboxylic acid (8.44 g, 98%) as a colorless solid. M.P. 149-152° C. (lit. m.p. 154-156° C.); IR (Di-ATR): 3000 (br, O—H), 2947 (C—H), 2862 (C—H), 1685 (C═O), 1284 (C—O), 1003 (C—F), 933, 734, 562 $cm^{-1}$; $^1H$ NMR (500 MHz, $CDCl_3$): δ 10.86 (1H, br s, OH), 2.37 (2H, br s, H6), 2.04 (2H, d, $^3J_{H3-F}$=6.0 Hz, H3), 1.88 (4H, m, H7), 1.83 (4H, m, H5), 1.62 (2H, d, $^3J_{H8-H6}$=3.0 Hz, H8) ppm; $^{13}C$ NMR (126 MHz, $CDCl_3$): δ 182.5 (C1), 92.1 (d, $^1J_{C4-F}$=184.9 Hz, C4), 44.9 (d, $^3J_{C2-F}$=10.1 Hz, C2), 43.5 (d, $^2J_{C3-F}$=20.1 Hz, C3), 41.9 (d, $^2J_{C7-F}$=17.6 Hz, C7), 37.5 (d, $^4J_{C5-F}$=1.3 Hz, C5), 34.9 (d, $^4J_{C8-F}$=1.3 Hz, C8), 30.9 (d, $^3J_{C6-F}$=10.0 Hz, C6) ppm; $^{19}F$ NMR (471 MHz, $CDCl_3$): δ −132.7 (s, C4-F) ppm; LRMS (−ESI): 197 ($[M-H]^+$, 100).

3-Fluoroadamantane-1-carboxamide. 3-Fluoroadamantane-1-carboxylic acid (1.37 g, 6.91 mmol) was coupled with ammonia using general procedure E, to obtain 3-fluoroadamantane-1-carboxamide (1.30 g, 95%) as a colorless solid. M.P. 144-147° C. (lit. m.p. 147-148 C); IR (Di-ATR): 3508 (N—H), 3418 (N—H), 3207 (N—H), 2941 (C—H), 2861 (C—H), 1633 (C═O), 1596 (N—H bend), 1001 (C—F), 934, 549 $cm^{-1}$; $^1H$ NMR (400 MHz, $CDCl_3$): δ 5.77 (1H, br s, NH), 5.61 (1H, br s, NH), 2.37 (2H, br d, J=2.4 Hz, H6), 1.99 (2H, d, $^3J_{H3-F}$=5.6 Hz, H3), 1.88 (4H, m, H7), 1.79 (4H, m, H5), 1.61 (2H, d, $^3J_{H8-H6}$=2.8 Hz, H8) ppm; $^{13}C$ NMR (101 MHz, $CDCl_3$): δ 178.7 (C1), 92.4 (d, $^1J_{C4-F}$=184.1 Hz, C4), 45.1 (d, $^3J_{C2-F}$=9.1 Hz, C2), 44.3 (d, $^2J_{C3-F}$=20.1 Hz, C3), 41.9 (d, $^2J_{C7-F}$=18.1 Hz, C7), 38.2 (d, $^4J_{C5-F}$=2.0 Hz, C5), 34.9 (d, $^4J_{C8-F}$=1.0 Hz, C8), 31.1 (d, $^3J_{C6-F}$=9.1 Hz, C6) ppm; $^{19}F$ NMR (376 MHz, $CDCl_3$): δ −132.2 (s, C4-F) ppm; LRMS (+ESI): 417 ($[2M+Na]^+$, 38), 220 ($[M+Na]^+$, 100).

(3-Fluoroadamantan-1-yl)methanamine. 3-Fluoroadamantane-1-carboxamide (1.16 g, 5.87 mmol) was reduced using general procedure F, to obtain (3-fluoroadamantan-1-yl)methanamine (0.92 g, 85%) as a colorless oil. IR (thin film): 2906, 2853, 1454, 1318, 1146, 1012, 937, 892, 765, 582, 537 $cm^{-1}$; $^1H$ NMR (500 MHz, $CDCl_3$): δ 2.44 (2H, s, H1), 2.30 (2H, br s, H6), 1.83 (4H, br quart, J=11.0 Hz, H7), 1.60 (2H, d, $^3J_{H3-F}$=5.0 Hz, H3), 1.56 (2H, m, H8), 1.48 (2H, s, $NH_2$), 1.39 (4H, br s, H5) ppm; $^{13}C$ NMR (126 MHz, $CDCl_3$): δ 93.3 (d, $^1J_{C4-F}$=182.4 Hz, C4), 53.6 (C1), 45.0 (d, $^3J_{C3-F}$=17.6 Hz, C3), 42.4 (d, $^2J_{C7-F}$=17.6 Hz, C7), 39.2 (d, $^2J_{C2-F}$=8.8 Hz, C2), 38.6 (d, $^4J_{C5-F}$=2.5 Hz, C5), 35.6 (d, $^4J_{C8-F}$=2.5 Hz, C8), 31.2 (d, $^3J_{C6-F}$=10.1 Hz, C6) ppm; $^{19}F$ NMR (471 MHz, $CDCl_3$): δ −131.4 (s, C4-F) ppm: LRMS (+ESI): 257 (32), 184 ($[M+H]^+$, 100).

2-Chloro-N-((3-fluoroadamantan-1-yl)methyl)-5-methoxybenzamide (Compound 3). (3-Fluoroadamantan-1-yl)methanamine (0.59 g, 3.2 mmol) and 2-chloro-5-methoxybenzoic acid (0.60 g, 3.2 mmol) were coupled using general procedure H, with $CH_2Cl_2$ as the solvent, to obtain 2-chloro-N-((3-fluoroadamantan-1-yl)methyl)-5-methoxybenzamide (0.85 g, 73%) as a colorless solid. M.P. 125-127° C.; IR (Di-ATR): 3204 (N—H), 3065 (Ar—H), 2928 (C—H), 2834 (C—H), 1640 (C═O), 1560, 1468, 1310, 1220 (Ar—O), 1021 (C—F), 891, 873, 814, 643 (C—Cl), 517 $cm^{-1}$; $^1H$ NMR (400 MHz, $CDCl_3$): δ 7.29 (1H, d, $^3J_{H12-H13}$=8.8 Hz, H12), 7.26 (1H, d, $^4J_{H15-H13}$=3.2 Hz, H15), 6.91 (1H, dd, $^3J_{H13-H12}$=9.0 Hz, $^4J_{H13-H15}$=3.0 Hz, H13), 6.38 (1H, br s, NH), 3.82 (3H, s, H16), 3.30 (2H, d, $^3J_{H1-NH}$=6.4 Hz, H1), 2.33 (2H, br s, H6), 1.86 (4H, m, H7), 1.73 (2H, d, $^3J_{H3-F}$=5.6 Hz, H3), 1.58 (2H, m, H8), 1.53 (4H, br s, H5) ppm; $^{13}C$ NMR (126 MHz, $CDCl_3$): δ 166.5 (s, C9), 158.7 (s, C14), 135.6 (s, C10), 131.3 (s, C12), 121.6 (s, C11), 118.2 (s, C13), 115.3 (s, C15), 92.9 (d, $^1J_{C4-F}$=183.6 Hz, C4), 55.9 (s, C16), 50.5 (s, C1), 45.4 (d, $^3J_{C3-F}$=17.6 Hz, C3), 42.2 (d, $^2J_{C7-F}$=17.6 Hz, C7), 39.1 (d, $^3J_{C2-F}$=8.8 Hz, C2), 38.9 (s, C5), 35.3 (s, C8), 31.1 (d, $^3J_{C6-F}$=10.1 Hz, C6) ppm; $^{19}F$ NMR (471 MHz, $CDCl_3$): δ −131.8 (s, C4-F) ppm; LRMS (+ESI): 725 ($[2M+Na]^+$, 22), 374 ($[M+Na]^+$, 100); HRMS (+ESI) Calc. for $C_{19}H_{23}{}^{37}ClFNNaO_2$ $[M+Na]^+$: 376.1264, found: 374.1264; Calc. for $C_{19}H_{23}{}^{35}ClFNNaO_2$ $[M+Na]^+$: 374.1294, found: 374.1293; Anal. ($C_{19}H_{23}ClFNO_2$): calc, C 64.86, H 6.59, N 3.98; found, C 64.90, H 6.54, N 3.90.

Example 3—Synthesis of Compound 2

3-Fluoro-5-hydroxyadamantane-1-carboxylic acid. 3-Fluoroadamantane-1-carboxylic acid (2.02 g, 10.2 mmol) was oxidized using general procedure A (refluxing for 2 h) to obtain a ~1:2 mixture (1.6 g) of starting material and 3-flouro-5-hydroxyadamantane-1-carboxylic acid. It is recommended that the mixture be used in the next step without purification due to solubility issues.

A portion of this mixture was purfied by column chromatography (1:1 ethyl acetate:hexane) for characterisation purposes. This resulted in recovery of 3-fluoroadamantane-1-carboxylic acid (24%) starting material and the desired 3-flouro-5-hydroxyadamantane-1-carboxylic acid (47%, 63% brsm) as a colorless solid. M.P. 186-189° C.; IR (Di-ATR): 3429 (O—H), 2940 (C—H), 2863 (C—H), 1707 (C═O), 1266 (C—O), 1228 (C—O), 1026 (C—F), 998, 876, 710, 539 $cm^{-1}$; $^1H$ NMR (400 MHz, $CD_3OD$): δ 2.42 (1H, m, H9), 1.92 (2H, d, J=5.2 Hz, H3), 1.84 (2H, J=5.2 Hz, H5), 1.79 (4H, br s, H7+H10), 1.71 (2H, br s, H8), 1.64 (2H, br s, H11) ppm; $^{13}C$ NMR (101 MHz, $CD_3OD$): δ 178.7 (d, $^4J_{C1-F}$=3.0 Hz, C1), 93.7 (d, $^1J_{C4-F}$=185.1 Hz, C4), 71.2 (d, $^3J_{C6-F}$=12.1 Hz, C6), 50.5 (d, $^2J_{C5-F}$=17.1 Hz, C5), 46.6 (d, $^3J_{C2-F}$=10.1 Hz, C2), 46.3 (s, C7), 44.2 (d, $^2J_{C3-F}$=20.1 Hz, C3), 43.6 (s, C11), 41.7 (d, $^2J_{C10-F}$=17.1 Hz, C10), 37.8 (d, $^4J_{C8-F}$=2.0 Hz, C8), 32.2 (d, $^3J_{C9-F}$=10.0 Hz, C9) ppm; $^{19}F$ NMR (376 MHz, $CD_3OD$): δ −136.8 (s, C4-F) ppm; LRMS (−ESI): 449 ($[2(M-H)+Na]^-$, 45), 427 ($[2M-H]^-$, 27), 213 ($[M-H]^-$, 100).

Methyl 3-fluoro-5-hydroxyadamantane-1-carboxylate. A ~1:2 mixture (1.0 g) of 3-fluoroadamantane-1-carboxylic acid and 3-fluoro-5-hydroxyadamantane-1-carboxylic acid was esterified and separated using general procedure B to obtain methyl 3-fluoro-5-hydroxyadamantane-1-carboxylate (0.69 g, 47% over 2 steps) as a white solid. Methyl 3-fluoroadamantane-1-carboxylate was also recovered (0.30 g, 22% over 2 steps). M.P. 52-54° C. (lit. m.p. 52-53° C.); IR (Di-ATR): 3526, 3224 (br, O—H), 2945 (C—H), 2913 (C—H), 2866 (C—H), 1708 (C═O), 1260 (C—O), 1229 (C—O), 1050, 1028 (C—F), 999, 512 $cm^{-1}$; $^1H$ NMR (500 MHz, $CDCl_3$): δ 3.69 (3H, s, H11), 2.46 (1H, m, H9), 1.98 (2H, d, J=5.0 Hz, H3), 1.91 (2H, J=6.0 Hz, H5), 1.87-1.78 (4H, m, H7+H10), 1.70 (2H, br s, H8), 1.62 (2H, m, H11) ppm; $^{13}C$ NMR (126 MHz, $CDCl_3$): δ 175.4 (d, $^4J_{C1-F}$=2.5 Hz, C1), 93.0 (d, $^1J_{C4-F}$=186.1 Hz, C4), 71.0 (d, $^3J_{C6-F}$=12.6 Hz, C6), 52.3 (s, C12), 49.8 (d, $^2J_{C5-F}$=17.6 Hz, C5), 45.7 (d, $^3J_{C2-F}$=11.3 Hz, C2), 45.5 (d, $^4J_{C7-F}$=1.3 Hz, C7), 43.0 (s, C11), 42.9 (d, $^2J_{C3-F}$=17.6 Hz, C3), 40.7 (d, $^2J_{C10-F}$=18.9 Hz, C10), 36.7 (d, $^4J_{C8-F}$=1.3 Hz, C8), 30.8 (d, $^3J_{C9-F}$=10.1 Hz, C9) ppm; $^{19}F$ NMR (471 MHz, $CDCl_3$): δ −136.4 (s, C4-F) ppm; LRMS (+APCI): 177 (50), 211 ($[M-OH]^+$, 100), 229 ([M+H]+, 50).

Methyl 3,5-difluoroadamantane-1-carboxylate. Methyl 3-fluoro-5-hydroxyadamantane-1-carboxylate (14.5 g, 63.5 mmol) was subjected to deoxyfluorination using general procedure C to obtain methyl 3,5-difluoroadamantane-1-carboxylate (11.17 g, 76%) as a colorless solid. M.P. 58-60° C. (lit. m.p. 52-53° C.); IR (Di-ATR): 2953 (C—H), 2940 (C—H), 2867 (C—H), 1728 (C═O), 1330, 1251, 1221 (C—O), 1039, 988, 947, 871, 544 $cm^{-1}$; $^1H$ NMR (500 MHz, $CDCl_3$): δ 3.70 (3H, s, H9), 2.52 (1H, m, H7), 2.10 (2H, br t, J=5.6 hz, H5), 2.00 (4H, br m, H3), 1.83 (4H, br s, H8), 1.71 (2H, s, H6) ppm; $^{13}C$ NMR (126 MHz, $CDCl_3$): δ 174.8 (s, C1), 92.9 (dd, $^1J_{C4-F}$=188.6 Hz, $^3J_{C4-C4'F}$=13.8 Hz, C4), 52.4 (s, C9), 47.6 (t, $^2J_{C5-F}$=18.9 Hz, C5), 45.9 (t, $^3J_{C2-F}$=10.7 Hz, C2), 42.9 (m, C3), 40.6 (m, H8), 36.6 (s, C6), 30.7 (t, $^3J_{C7-F}$=10.7 Hz, C7) ppm; $^{19}F$ NMR (471 MHz, $CDCl_3$): δ −137.1 (s, C4-F) ppm; LRMS (+APCI): 212 ($[M-F]^+$, 32), 231 ($[M+H]^+$, 100).

3,5-Difluoroadamantane-1-carboxylic acid. Methyl 3,5-difluoroadamantane-1-carboxylate (5.24 g, 22.8 mmol) was saponified using general procedure D to obtain 3,5-difluoroadamantane-1-carboxylic acid (4.74 g, 96%) as a colorless solid. M.P. 161-163° C. (lit. m.p. 162-164° C.); IR (Di-ATR): 2949 (C—H), 2900 (br, O—H), 2865 (C—H), 1709 (C═O), 1330, 1276, 1026, 991 (C—F), 947, 877, 719, 544 $cm^{-1}$; $^{1}H$ NMR (500 MHz, $CDCl_3$): δ 10.75 (1H, br s, OH), 2.55 (1H, m, H7), 2.12 (2H, t, J=5.3 hz, H5), 2.03 (4H, m, H3), 1.85 (4H, m, H8), 1.75 (2H, br s, H6) ppm; $^{13}C$ NMR (126 MHz, $CDCl_3$): δ 180.7 (t, $^{4}J_{C1-F}$=2.5 Hz, C1), 92.8 (dd, $^{1}J_{C4-F}$=188.8 Hz, $^{3}J_{C4-C4'F}$=14.0 Hz, C4), 47.5 (t, $^{2}J_{C5-F}$=19.5 Hz, C5), 45.7 (t, $^{3}J_{C2-F}$=10.7 Hz, C2), 42.6 (m, C3), 40.5 (m, H8), 36.4 (t, $^{4}J_{C6-F}$=1.3 Hz, C6), 30.7 (t, $^{3}J_{C7-F}$=10.7 Hz, C7) ppm; $^{19}F$ NMR (471 MHz, $CDCl_3$): δ −137.3 (s, C4-F) ppm; LRMS (−ESI): 248 ($[M-H+MeOH]^-$, 100), 216 ($[M-H]^-$, 90).

3,5-Difluoroadamantane-1-carboxamide. 3,5-Difluoroadamantane-1-carboxylic acid (2.00 g, 9.25 mmol) was coupled with ammonia using general procedure E to obtain 3,5-difluoroadamantane-1-carboxamide (1.84 g, 93%) as a colorless solid. M.P. 149-152° C.; IR (Di-ATR): 3477 (N—H), 3346 (N—H), 3290 (N—H), 3200 (br), 2948 (C—H), 2921 (C—H), 2867 (C—H), 1667 (C═O), 1611, 1332, 1127, 1018, 958 (C—F), 944, 503, 414 $cm^{-1}$; $^{1}H$ NMR (400 MHz, $CD_3OD$): δ 2.51 (1H, m, H7), 2.05 (2H, t, J=5.6 hz, H5), 1.95 (4H, m, H3), 1.83 (4H, m, H8), 1.71 (2H, br s, H6) ppm; $^{13}C$ NMR (101 MHz, $CD_3OD$): δ 180.0 (s, C1), 93.9 (dd, $^{1}J_{C4-F}$=187.8 Hz, $^{3}J_{C4-C4'F}$=13.8 Hz, C4), 48.4 (t, $^{2}J_{C5-F}$=19.1 Hz, C5), 47.2 (t, $^{3}J_{C2-F}$=10.1 Hz, C2), 44.1 (m, C3), 41.4 (m, H8), 37.7 (t, $^{4}J_{C6-F}$=2.0 Hz, C6), 32.2 (t, $^{3}J_{C7-F}$=10.6 Hz, C7) ppm; $^{19}F$ NMR (376 MHz, $CD_3OD$): δ −137.4 (s, C4-F) ppm; LRMS (+ESI): 453 ($[2M+Na]^+$, 100), 238 ($[M+H]^+$, 50).

(3,5-Difluoroadamantan-1-yl)methanamine. 3,5-Difluoroadamantane-1-carboxamide (1.71 g, 7.96 mmol) was reduced using general procedure F, to obtain (3,5-difluoroadamantan-1-yl)methanamine (1.54 g, 96%) as a colorless oil. IR (Di-ATR): 3300 (br, N—H), 2918 (C—H), 2865 (C—H), 1551 (N—H bend), 1416, 1330, 990 (C—F), 944, 544 $cm^{-1}$; $^{1}H$ NMR (400 MHz, $CDCl_3$): δ 2.53 (2H, s, H1), 2.47 (1H, m, H7), 2.05 (2H, t, J=5.4 hz, H5), 1.78 (4H, m, H3), 1.60 (4H, m, H8), 1.31 (2H, br s, H6), 1.15 (2H, s, $NH_2$) ppm; $^{13}C$ NMR (126 MHz, $CDCl_3$): δ 93.7 (dd, $^{1}J_{C4-F}$=187.6 Hz, $^{3}J_{C4-C4'F}$=13.6 Hz, C4), 52.4 (s, C1), 47.8 (t, $^{2}J_{C5-F}$=18.6 Hz, C5), 43.9 (m, C3), 41.0 (m, C8), 40.8 (t, $^{3}J_{C2-F}$=9.1 Hz, C2), 37.3 (t, $^{4}J_{C6-F}$=2.0 Hz, C6), 30.7 (t, $^{3}J_{C7-F}$=10.6 Hz, C7) ppm; $^{19}F$ NMR (376 MHz, $CDCl_3$): δ −136.3 (s, C4-F) ppm; LRMS (+ESI): 415 (30), 360 (95), 317 (35), 202 ($[M+H]^+$, 100).

2-Chloro-N-((3,5-difluoroadamantan-1-yl)methyl)-5-methoxybenzamide (Compound 2). (3,5-Difluoroadamantan-1-yl)methanamine (0.22 g, 1.07 mmol) and 2-chloro-5-methoxybenzoic acid (0.23 g, 1.25 mmol) were coupled using general procedure H with $CH_2Cl_2$ as the solvent to obtain 2-chloro-N-((3,5-difluoroadamantan-1-yl)methyl)-5-methoxybenzamide (0.35 g, 88%) as a colorless solid. M.P. 142-144° C.; IR (Di-ATR): 3246 (N—H), 3077 (Ar—H), 2918 (C—H), 2861 (C—H), 1646 (C═O), 1549, 1332, 1295, 1235 (Ar—O)), 991 (C—F), 936, 809, 646 (C—Cl), 545 $cm^{-1}$; $^{1}H$ NMR (400 MHz, $CDCl_3$): δ 7.29 (1H, d, $^{3}J_{H12-H13}$=8.8 Hz, H12), 7.24 (1H, d, $^{4}J_{H15-H13}$=2.8 Hz, H15), 6.91 (1H, dd, $^{3}J_{H13-H12}$=8.8 Hz, $^{4}J_{H13-H15}$=3.2 Hz, H13), 6.44 (1H, br t, NH), 3.82 (3H, s, H16), 3.39 (2H, d, $^{3}J_{H1-NH}$=6.4 Hz, H1), 2.50 (1H, m, H7), 2.08 (2H, t, $^{3}J_{H5-F}$=5.2 Hz, H5), 1.90-1.70 (8H, m, H3+H8), 1.25 (2H, br s, H6) ppm; $^{13}C$ NMR (101 MHz, $CDCl_3$): δ 166.5 (s, C9), 158.7 (s, C14), 135.4 (s, C10), 131.3 (s, C12), 121.5 (s, C11), 118.3 (s, C13), 115.4 (s, C15), 93.3 (dd, $^{1}J_{C4-F}$=188.6 Hz, $^{3}J_{C4-C4'F}$=13.6 Hz, C4), 55.9 (s, C16), 49.4 (s, C1), 47.7 (t, $^{2}J_{C5-F}$=18.6 Hz, C5), 44.3 (m, C3), 40.8 (m, C8), 40.6 (t, $^{3}J_{C2-F}$=9.6 Hz, C2), 37.7 (s, C6), 30.6 (t, $^{3}J_{C7-F}$=10.6 Hz, C7) ppm; $^{19}F$ NMR (376 MHz, $CDCl_3$): δ −136.7 (s, C4-F) ppm; LRMS (+ESI): 761 ($[2M+Na]^+$, 9), 392 ($[M+Na]^+$, 100); HRMS (+ESI) Calc. for $C_{19}H_{22}{}^{37}ClF_2NNaO_2$ $[M+Na]^+$: 394.1170, found: 394.1169; Calc. for $C_{19}H_{22}{}^{35}ClF_2NNaO_2$ $[M+Na]^+$: 392.1199, found: 392.1199; Anal. ($C_{19}H_{22}ClF_2NO_2$): calc, C 61.71, H 6.00, N 3.79; found, C 61.70, H 5.98, N 3.74.

Example 4—Synthesis of Compound 1

3,5-Difluoro-7-hydroxyadamantane-1-carboxylic acid. 3,5-Difluoroadamantane-1-carboxylic acid (4.71 g, 21.90 mmol) was oxidized using general procedure A (refluxing for 21 h), to obtain a ~1:1 mixture (4.83 g) of starting material and the 3,5-diflouro-7-hydroxyadamantane-1-carboxylic acid. It is recommended that the mixture be used in the next step without purification due to solubility issues.

A portion of this mixture was purified by column chromatography (1:1 ethyl acetate:hexane) for characterisation purposes. This resulted in recovery of the 3,5-difluoroadamantane-1-carboxylic acid 31 (44%) starting material and the desired 3,5-diflouro-5-hydroxyadamantane-1-carboxylic acid S12 (51%, 63% brsm) as a colorless solid. M.P. 200-204° C.; IR (Di-ATR): 3422 (O—H), 2962 (C—H), 1704 (C═O), 1338, 1022 (C—O), 963 (C—F), 700, 543 $cm^{-1}$;): 3429 (O—H), 2940 (C—H), 2863 (C—H), 1707 (C═O), 1266 (C—O), 1228 (C—O), 1026 (C—F), 998, 876, 710, 539 $cm^{-1}$; $^{1}H$ NMR (400 MHz, $CD_3OD$): δ 2.12-1.99 (2H, m. H5), 1.93 (4H, br s, H3), 1.87 (4H, m, H8), 1.76 (s, H6) ppm; $^{13}C$ NMR (101 MHz, $CD_3OD$): δ 177.3 (s, C1), 93.4 (dd, $^{1}J_{C4-F}$=188.1 Hz, $^{3}J_{C4-C4'F}$=15.1 Hz, C4), 71.3 (t, $^{3}J_{C7-F}$=13.6 Hz, C7), 49.5-48.8 (m, obstructed by solvent, C8), 47.4 (t, $^{2}J_{C5-F}$=19.6 Hz, C5), 45.4 (s, C6), 44.9 (t, $^{3}J_{C2-F}$=12.1 Hz, C2), 43.2 (m, C3) ppm; $^{19}F$ NMR (376 MHz, $CD_3OD$): δ −142.5 (s, C4-F) ppm; LRMS (−ESI): 231.2 ($[M-H]^-$, 100).

Methyl 3,5-difluoro-7-hydroxyadamantane-1-carboxylate. A ~1:1 mixture (4.83 g) of 3,5-difluoroadamantane-1-carboxylic acid and 3,5-diflouro-7-hydroxyadamantane-1-carboxylic acid was esterified and separated using general procedure B to obtain methyl 3,5-difluoro-7-hydroxyadamantane-1-carboxylate 35 (2.68 g, 50% over 2 steps, 88% brsm) as a white solid. Methyl 3,5-difluoroadamantane-1-carboxylate 30 was also recovered (2.19 g, 43% over 2 steps). M.P. 96-97° C. (lit. m.p. 100-101° C.); IR (Di-ATR): 3522 (O—H), 3208, 2958 (C—H), 1709 (C═O), 1338, 1271 (C—O), 1228 (C—O), 1014, 957, 545 $cm^{-1}$; $^{1}H$ NMR (500 MHz, $CDCl_3$): δ 3.61 (3H, s, H9), 1.99 (1H, m, H5a), 1.92 (1H, m, H5b), 1.89-1.79 (8H, m, H3, H8), 1.68 (2H, br s, H6) ppm; $^{13}C$ NMR (126 MHz, $CDCl_3$): δ 174.1 (t, $^{4}J_{C1-F}$=2.6 Hz, C1), 92.3 (t, $^{1}J_{C4-F}$=188.6 Hz, $^{3}J_{C4-F'}$=15.3 Hz, C4), 70.0 (t, $^{3}J_{C7-F}$=13.8 Hz, C7), 52.3 (s, C9), 48.4 (m, C8), 46.4 (t, $^{2}J_{C5-F}$=19.5 Hz, C5), 44.3 (s, C6), 43.7 (t, $^{3}J_{C2-F}$=11.9 Hz, C2), 41.9 (m, C3) ppm; $^{19}F$ NMR (471 MHz, $CDCl_3$): δ −141.6 (s, C4-F) ppm; LRMS (+APCI): 247 ($[M+H]^+$, 100).

Methyl 3,5,7-trifluoroadamantane-1-carboxylate. Methyl 3,5-difluoro-7-hydroxyadamantane-1-carboxylate (0.32 g, 1.37 mmol) was subjected to deoxyfluorination using general procedure C to obtain methyl 3,5,7-trifluoroadamantane-1-carboxylate 36 (0.26 g, 80%) as a colorless solid. M.P. 111-112° C. (lit. m.p. 109-110° C.)[2]; IR (Di-ATR): 2957 (C—H), 2877 (C—H), 1732 (C═O), 1335, 1255, 1222 (C—O), 1015, 961 (C—F), 740, 553, 424 $cm^{-1}$; $^{1}H$ NMR (500 MHz, $CDCl_3$): δ 3.74 (3H, s, H6), 2.19-2.04 (6H, m, H5), 1.99 (6H, br s, H3) ppm; $^{13}C$ NMR (126 MHz, $CDCl_3$): δ 173.5 (quart, $^4J_{C1-F}$=3.4 Hz, C1), 91.9 (dt, $^1J_{C4-F}$=191.3 Hz, $^3J_{C4-F}$=15.3 Hz, C4), 52.8 (s, C6), 46.5 (m, C5), 43.4 (quart, $^3J_{C2-F}$=11.7 Hz, C2), 42.1 (m, C3) ppm; $^{19}$F NMR (471 MHz, $CDCl_3$): δ −143.4 (s, C4-F) ppm; LRMS (+APCI): 229 ($[M-F]^+$. 20), 249 ($[M+H]^+$, 100).

3,5,7-Trifluoroadamantane-1-carboxylic acid. Methyl 3,5,7-trifluoroadamantane-1-carboxylate 36 (1.20 g, 4.82 mmol) was saponified using general procedure D to obtain 3,5,7-trifluoroadamantane-1-carboxylic acid 37 (1.12 g, 99%) as a colorless solid. M.P. 197-198° C. (lit. m.p. 198-199° C.); IR (Di-ATR): 2971 (C—H), 2900 (br, OH), 1700 (C═O), 1338, 1297, 1263, 1021, 964, 858, 717, 544, 423 $cm^{-1}$; $^1$H NMR (500 MHz, $CDCl_3$): δ 11.16 (1H, br s, COOH), 2.22-2.06 (6H, m, H5), 2.02 (6H, br s, H3) ppm; $^{13}$C NMR (126 MHz, $CDCl_3$): δ 179.6 (quart, $^4J_{C1-F}$=4.2 Hz, C1), 91.7 (dt, $^1J_{C4-F}$=191.1 Hz, $^3J_{C4-F}$=15.1 Hz, C4), 46.5 (m, C5), 43.3 (quart, $^3J_{C2-F}$=12.2 Hz, C2), 41.8 (m, C3) ppm; $^{19}$F NMR (471 MHz, $CDCl_3$): δ −143.4 (s, C4-F) ppm; LRMS (−ESI): 233 ($[M-H]^-$, 100).

3,5,7-Trifluoroadamantane-1-carboxamide. 3,5,7-Trifluoroadamantane-1-carboxylic acid 37 (1.12 g, 4.78 mmol) was coupled with ammonia using general procedure E to obtain 3,5,7-trifluoroadamantane-1-carboxamide (0.94 g, 84%) as a colorless solid. M.P. 153-156° C.; IR (Di-ATR): 3506 (N—H), 3399 (N—H), 3354, 3164, 2961 (C—H), 1665 (C═O), 1336, 1009, 959, 546, 421 $cm^{-1}$; $^1$H NMR (500 MHz, $CD_3OD$): δ 2.11 (6H, m, H5), 1.96 (6H, br s, H3) ppm; $^{13}$C NMR (126 MHz, $CD_3OD$): δ 178.4 (t, $^4J_{C1-F}$=2.5 Hz, C1), 93.1 (dt, $^1J_{C4-F}$=190.3 Hz, $^3J_{C4-C4'F}$=15.3 Hz, C4), 47.4-46.8 (m, C5), 43.5-42.9 (m, C2+C3) ppm; $^{19}$F NMR (471 MHz, $CD_3OD$): δ −143.7 (s, C4-F) ppm; LRMS (−ESI): 232 ($[M-H]^-$, 100).

(3,5,7-Trifluoroadamantan-1-yl)methanamine. 3,5,7-Trifluoroadamantane-1-carboxamide (0.94 g, 4.03 mmol) was reduced using general procedure F to obtain (3,5,7-trifluoroadamantan-1-yl)methanamine 38 (0.88 g, 93%) as a low-melting, colourless solid. IR (Di-ATR): 2960, 2923, 2870, 1332, 1014, 960, 549, 424 $cm^{-1}$; $^1$H NMR (400 MHz, $CDCl_3$): δ 2.63 (2H, s, C1), 2.09 (6H, m, H5), 1.61 (6H, br s, H3), 1.07 (2H, br s, $NH_2$) ppm; $^{13}$C NMR (101 MHz, $CDCl_3$): δ 92.5 (dt, $^1J_{C4-F}$=190.1 Hz, $^3J_{C4-C4'F}$=15.1 Hz, C4), 51.5 (d, $^4J_{C1-F}$=2.0 Hz, C1), 46.9 (m, C5), 43.1 (m, C3), 38.6 (quart, $^3J_{C2-F}$=10.1 Hz, C2) ppm; $^{19}$F NMR (376 MHz, $CDCl_3$): δ −143.0 (s, C4-F) ppm; LRMS (+ESI): 220 ($[M+H]^+$, 100).

2-Chloro-N-((3,5,7-trifluoroadamantan-1-yl)methyl)-5-methoxybenzamide (Compound 1). (3,5,7-Trifluoroadamantan-1-yl)methanamine (0.10 g, 0.46 mmol) and 2-chloro-5-methoxybenzoic acid 27 (0.01 g, 0.54 mmol) were coupled using general procedure H, with $CH_2Cl_2$ as the solvent, to obtain 2-chloro-N-((3,5,7-trifluoroadamantan-1-yl)methyl)-5-methoxybenzamide (0.17 g, 91%) as a colorless solid. M.P. 196-198° C.; IR (Di-ATR): 3273 (N—H), 2959 (Ar—H), 2918 (C—H), 2850 (C—H), 1646 (C═O), 1549, 1335, 1295, 1237 (Ar—O), 1015 (C—F), 943, 811, 647 (C—Cl), 550, 423 $cm^{-1}$; $^1$H NMR (500 MHz, $CDCl_3$): δ 7.29 (1H, d, $^3J_{H9-H10}$=9.0 Hz, H9), 7.22 (1H, d, $^4J_{H12-H10}$=3.0 Hz, H12), 6.92 (1H, dd, $^3J_{H10-H9}$=9.0 Hz, $^4J_{H10-H12}$=3.0 Hz, H10), 6.51 (1H, br t, NH), 3.82 (3H, s, H13), 3.46 (2H, d, $^3J_{H1-NH}$=6.5 Hz, H1), 2.10 (6H, m, H5), 1.72 (6H, s, H3) ppm; $^{13}$C NMR (126 MHz, $CDCl_3$): δ 166.7 (s, C6), 158.7 (s, C11), 135.1 (s, C7), 131.4 (s, C9), 121.5 (s, C8), 118.4 (s, C10), 115.4 (s, C12), 92.1 (dt, $^1J_{C4-F}$=190.3 Hz, $^3J_{C4-C4'F}$=15.4 Hz, C4), 55.9 (s, C13), 48.5 (d, $^4J_{C1-F}$=2.5 Hz, C1), 46.6 (m, C5), 43.4 (m, C3), 38.5 (quart, $^3J_{C2-F}$=10.9 Hz, C2) ppm; $^{19}$F NMR (471 MHz, $CDCl_3$): δ −143.3 (s, C4-F) ppm; LRMS (+ESI): 797 ($[2M+Na]^+$, 13), 410 ($[M+Na]^+$, 100); HRMS (+ESI) Calc. for $C_{19}H_{21}{}^{37}ClF_3NO_2$ $[M+Na]^+$: 412.1076, found: 412.1076; Calc. for $C_{19}H_{21}{}^{35}ClF_3NO_2$ $[M+Na]^+$: 410.1105, found: 410.1105; Anal. ($C_{19}H_{21}ClF_3NO_2$): calc, C 58.84, H 5.46, N 3.61; found, C 58.85, H 5.49, N 3.65.

Example 5—Determination of Lipophilicity

Lipophilicity of the compounds was evaluated by an experimentally derived Log $D_{7.4}$ value determined by a HPLC method.[1] It is preferred that the lipophilicity of the compounds is as low as possible.

High Performance Liquid Chromatography was performed on a Waters 2695 Separations module equipped with the Waters Alliance Series Column Heater (set at 30° C.) and Waters 2996 Photodiode Array (PDA) Detector. Samples were resolved on a Waters Sunfire™ C18 5 μm column (2.1×150 mm) using an isocratic flow of 65 v/v % methanol in 50 mM sodium phosphate buffer (pH 7.4) at a flowrate of 0.3 mL/min. Standards and samples were dissolved in the elution solvent mixture and then filtered prior to injection. Data acquisition and processing was performed with the Waters Empower 2 software and Microsoft Excel™ was used for data analysis. All standards and samples were analyzed in triplicate.

The retention times (RET) of acetone (log $D_{7.4}$ −0.24), aniline (log $D_{7.4}$ 0.90), phenol (log $D_{7.4}$ 1.50), toluene (log $D_{7.4}$ 2.73), cumene (log $D_{7.4}$ 3.66), triphenylamine (log $D_{7.4}$ 5.74) and hexachlorobenzene (log $D_{7.4}$ 6.35) were plotted against their literature log $D_{7.4}$ values[2] to obtain a calibration curve. An exponential curve was obtained (FIG. 1) which was fitted to the equation [Log $D_{7.4}$=0.8342(RET)+1.7393] with an $R^2$ of 0.97.

The RET from three injections was averaged with the log $D_{7.4}$ value extrapolated from the equation found in FIG. 1. The results are presented in Table 1 below.

TABLE 1

Average RET and log$D_{7.4}$ values

| Compound | Average (min)[a] | RET log$D_{7.4}$[b] |
|---|---|---|
| 31 | 19.69 ± 0.08 | 4.23 |
| 3 | 6.27 ± 0.03 | 3.27 |
| 2 | 3.77 ± 0.02 | 2.85 |
| 1 | 3.68 ± 0.02 | 2.83 |

[a]average retention time ± standard error based on the conditions outlined above.
[b]Log$D_{7.4}$ calculated from the equation Log$D_{7.4}$ = 0.8342(RET) + 1.7393

Compound 31 in the above table is a comparator compound having the following structure:

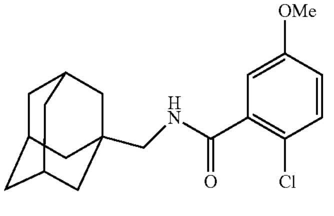 [SMILES: COc1ccc(Cl)c(C(=O)NCC23CC4CC(CC(C4)C2)C3)c1]

Each of compounds 1, 2 and 3 were found to be less lipophilic than compound 31.

Example 6—In Vitro Structure-Activity Relationship (SAR) Assays

General Experimental

Human monocytic leukaemia cells (THP-1) were obtained from the American Type Culture Collection (ATCC) and were grown in RPMI 1640 medium (Invitrogen), supplemented with penicillin (100 U/mL), streptomycin (100 μg/mL) and 10% (v/v) heat-inactivated fetal bovine serum (FBS). HEK293T cells transfected with cDNA for the human (HEK-hP2X7) or mouse $P2X_7$ (HEK-m$P2X_7$) receptor (a kind gift from Dr Leanne Stokes and Prof. Jim Wiley) were cultured in DMEM/F12 with 10% FBS and 500 μg/mL G418 (all from Invitrogen). Cells were cultured in 75 $cm^2$ flasks and incubated at 37° C. in a 5% $CO_2$ humidified atmosphere, maintained in log phase of growth and passaged when cell density reached $1\times10^6$ cells/mL (every 2-3 days).[3]

Yo-Pro Uptake Assay for Pore Formation $P2X_7R$ pore formation was assessed by agonist-induced uptake of the Yo-Pro-1 iodide dye. Cells were plated in 96-well black-walled, clear bottom plates in the presence of lipopolysaccharide (LPS, 25 ng/ml) and interferon-gamma (IFNγ, 10 ng/mL). Following an overnight incubation (16 h) required for THP-1 differentiation, cells were pre-incubated with various compound concentrations (diluted in DMSO) or control in culture medium (DMSO final concentration of 0.1%) for 30 min. Final treatments (in triplicate) were made up in phosphate buffered saline (PBS), without divalent cations, containing PRO®-1 dye (2 μM). Cells were washed once in pre-warmed PBS and treatments were added to cells, with or without 2'(3')-O-(4-benzoylbenzoyl)adenosine 5'-triphosphate (BzATP, 100 μM) as agonist. Dye uptake was measured at 37° C. using a fluorescence plate reader (BMG Labtech); with data read at $\lambda_{Ex485nm}/\lambda_{Em520nm}$ at 30 sec intervals over a 70 min period. Maximal intensity was determined by the $EC_{70}$ value of agonist concentration (100 μM BzATP) and each compound concentration was expressed as a percentage of this maximal intensity to account for any variability between single experiments. $IC_{50}$ values were determined from concentration-response curves derived from a four-parameter variable slope, analyzed in GraphPad Prism® (San Diego, CA).

Calcium Influx Assay

Figure 3:
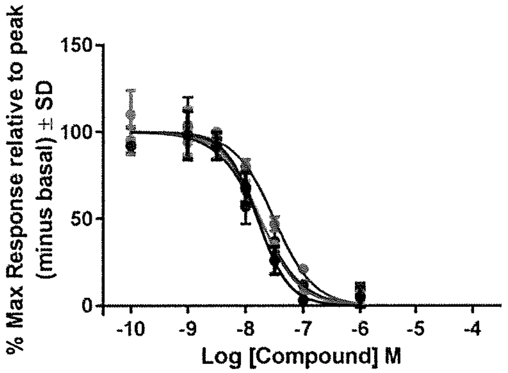
FIG. 3: Inhibition of human (A) and mouse (B) $P2X_7R$-induced $Ca^{2+}$ influx, demonstrating that degree of susceptibility to reduced potency on mouse $P2X_7R$ depends on fluorination number. In this figure, "1" refers to compound 31, "28" refers to compound 3, "33" refers to compound 2 and "34" refers to compound 1.
Figure 3:
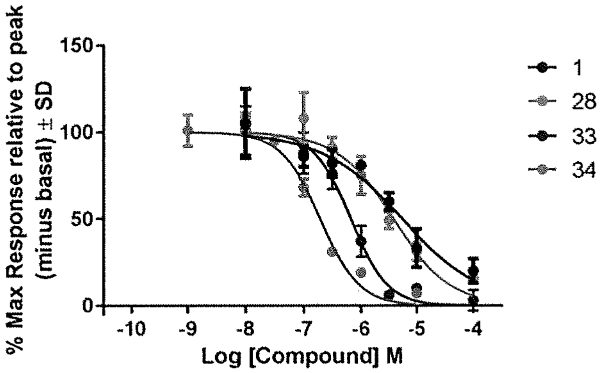

HEK-hP2X7 or HEK-mP2X7 cells were harvested using trypsin (0.05%) with EDTA (0.03%). Cells were loaded with Fluo-4 AM (1 μM) in HBSS buffer at 37° C. for 30 min, inverting every 5 mins. Cells were then washed twice with assay buffer (NaCl 137 mM, KCl 1.8 mM, $KH_2PO_4$ 1.2 mM, $MgSO_4$ 1.2 mM, $NaHCO_3$ 5.2 mM, $CaCl_2$ 1.6 mM, glucose 6 mM, HEPES 20 mM, pH 7.3), centrifuging between washes at 1200 rpm for 5 mins. Cells were resuspended a final time in assay buffer and seeded into black-walled 96 well clear-bottom plates at a density of $5\times10^4$ cells/well. Prewarmed (37° C.) assay buffer containing the test compound (concentrations of 0.1 nM to 1 μM) or vehicle (DMSO) were added and 3 min preincubation followed. Fluorescence was read using a BMG POLARstar Omega ($\lambda_{ex}$=485-12, $\lambda_{em}$=520), with 20 sec baseline measurements for each well taken followed by injection of BzATP (final concentration 100 μM) or vehicle (ultrapure water). Fluorescence was then monitored every 5 s for 5 min total monitoring. To determine the $IC_{50}$, data from each experiment were fitted using a 4-parameter logistic equation using Graphpad Prism. Data were normalized to the peak response seen with BzATP alone and the basal response seen due to injection of vehicle (see FIG. 3).

Membrane Preparation for Radioligand Binding Assay

HEK-h$P2X_7$ cells were harvested using 0.02% EDTA (w/v) in PBS, resuspended in homogenization buffer (Tris HCl 50 mM, NaCl 140 mM, EDTA 5 mM, pH 7.4, 4° C.) and homogenized via 2 bursts of 10 s on the high speed setting of an Ultra-Turrax hand-held homogenizer (IKA Werke, Staufen, Germany). Homogenates were centrifuged at 48 000 g for 20 min at 4° C., the supernatant discarded and the pellet resuspended in Tris HCl 50 mM (pH 7.4 at 4° C.). Two additional spins at 48 000 g followed, discarding the supernatant each time and resuspending the pellet in 50 mM Tris HCl each time. Protein content was determined via bicinchoninic acid (BCA) assay (Pierce Biotechnology Inc., Rockford), the membrane solution supplemented with 0.1% bovine serum albumin (BSA) and stored at −80° C.

Radioligand Binding Assay

Figure 4:
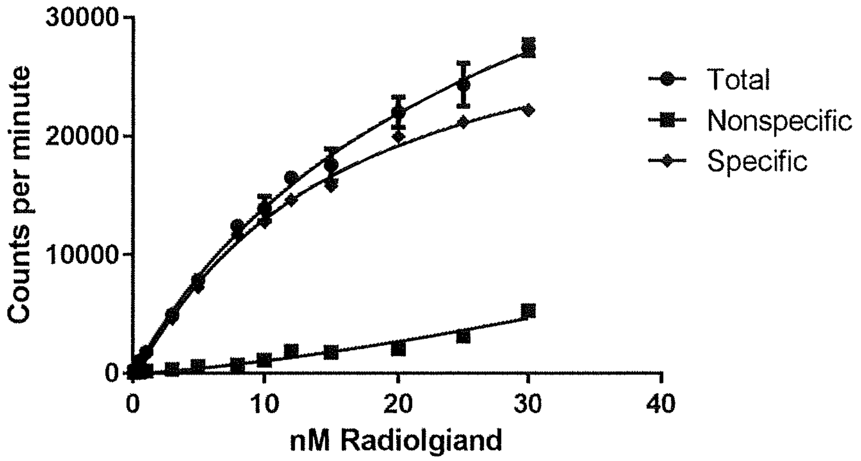
FIG. 4: Saturation radioligand binding curves used to derive $K_d$ and $B_{max}$ for $[^3H]$-compound 31.
Figure 5:
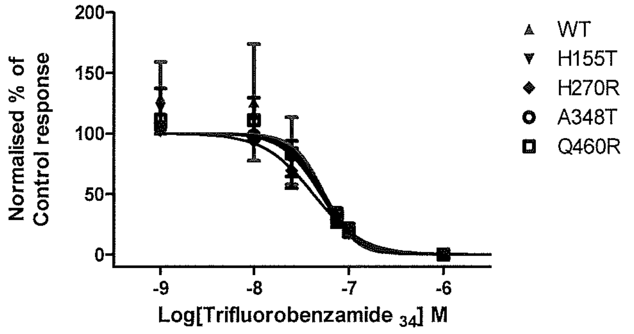
FIG. 5: Potency of compound 1 against functionally-characterized polymorphisms of $hP2X_7$ in response to A) 1 mM ATP or B) 100 μM BzATP.
Figure 5:
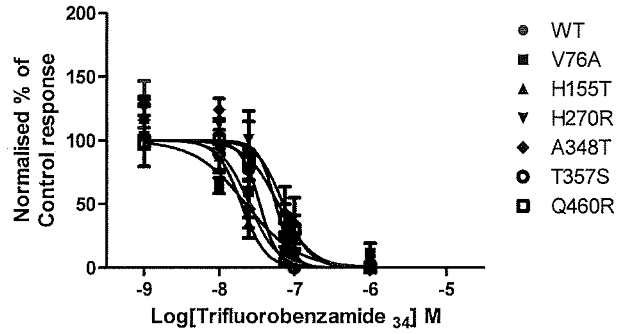

For saturation radioligand binding, membranes (30 μg $well^{-1}$) from HEK-h$P2X_7$ were incubated with [$^3$H]-Compound 31 (conc. 0.1-30 nM) in RLB assay buffer (Tris HCl 50 mM, 0.1% BSA, pH 7.4) for 2 h at room temperature. Non-specific binding was determined using 10 μM of Compound 31. The incubation was terminated by rapid filtration through a glass fibre filter (GF/B; Millipore, Ireland), pre-soaked beforehand with 0.3% PEI) and washed 10 times with 50 mM Tris HCl (4° C.). The filters were then allowed to dry overnight before adding Microscint-0 scintillation cocktail (Perkin Elmer). The amount of radioactivity retained on the filters was determined using a Microbeta2 2450 Microplate Counter (Perkin Elmer). For $K_d$ and $B_{max}$ determination the specific binding was calculated (total binding minus non-specific binding) and analyzed using a one-site binding model (hyperbolic). The total binding and non-specific binding were also plotted for comparison (see FIG. 4). Competition studies with the appropriate competitor were performed under similar conditions using a fixed concentration of [$^3$H]-Compound 31 (14 nM) or vehicle (ethanol). Using the $K_d$ of compound 31 determined in saturation assays, the $K_i$ of each competitor was fitted directly using non-linear regression, assuming one-site binding and a hill slope of 1. The extra sum of squares F-test was used to evaluate three potential models to fit the data; a one-site fit (with hill slope constrained to 1), a one-site fit (with hill slope as a variable) and a two-site fit. Association studies were performed using 14 nM [$^3$H]-Compound 31 and dissociation studies using 18 nM [$^3$H]-Compound 31 with incubations up to 240 min. Dissociation was triggered via dilution and the addition of 10 μM Compound 31 or vehicle (DMSO). The $K_{off}$ from dissociation studies was calculated using non-linear regression (exponential model) and then, in combination with the data from association studies, used to calculate the $K_{on}$. All data were analyzed using GraphPad Prism 5.

A summary of the SAR results is presented below in Table 2.

TABLE 2

SAR for selected compounds

| Compound | $LogD_{7.4}$ | Dye uptake $IC_{50}$ $hP2X_7R$ (nM)[a] | Calcium influx $IC_{50}$ (nM)[b] $hP2X_7R$ | Calcium influx $IC_{50}$ (nM)[b] $mP2X_7R$ | Binding affinity $K_i$ (nM)[c] | LLE[d] |
|---|---|---|---|---|---|---|
| 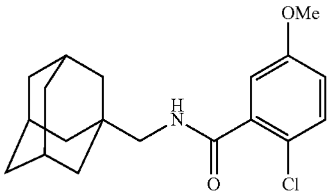 [SMILES: COc1ccc(Cl)c(C(=O)NCC23CC4CC(CC(C4)C2)C3)c1] | 4.23 | 10.5 ± 3.1 | 25.7 ± 8.7 | 1905 ± 905 | 8.5 ± 0.6 | 3.75 |
| 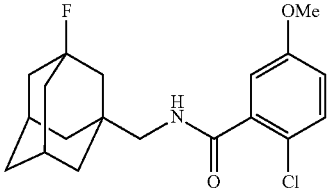 [SMILES: COc1ccc(Cl)c(C(=O)NCC23CC4CC(CC(F)(C4)C2)C3)c1] | 3.27 | 25.1 ± 2.7 | 17.4 ± 2.9 | 1513 ± 339 | 21.9 ± 0.5 | 4.33 |
| 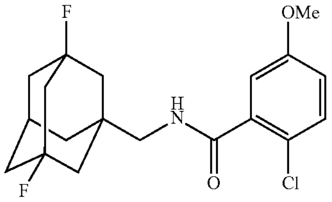 [SMILES: COc1ccc(Cl)c(C(=O)NCC23CC4CC(F)(CC(F)(C4)C2)C3)c1] | 2.85 | 30.9 ± 8.0 | 10.0 ± 4.0 | 575 ± 108 | 23 ± 5 | 4.66 |
| 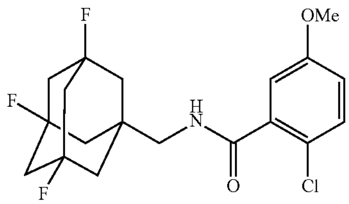 [SMILES: COc1ccc(Cl)c(C(=O)NCC23CC4(F)CC(F)(CC(F)(C4)C2)C3)c1] | 2.83 | 33.9 ± 11 | 24.5 ± 5.5 | 158 ± 44 | 32 ± 5 | 4.64 |

[a] $IC_{50}$ values were the mean values (n >4) ± standard deviation derived from a dye uptake assay with THP-1 cells.

[b] $IC_{50}$ values were the mean values (n >3) ± standard deviation derived from calcium influx in HEK cells expressing $hP2X_7R$ or $mP2X_7R$.

[c] Binding affinities ($K_i$) were the mean values (n >3) ± standard deviation derived from the displacement of tritium-labeled benzamide 31-$t_3$ in HEK cells expressing $hP2X_7R$.

[d] LLE = $pIC_{50}$(from dye uptake) LogD − (from HPLC)

All of the fluorinated benzamides exhibited a greater inhibitory effect ($IC_{50}$ 10-25 nM) than in the dye uptake assay ($IC_{50}$ 25-34 nM). In addition, these results were equal to or better than compound 31 ($IC_{50}$ 26 nM). All fluorinated benzamides exhibited comparative binding affinities (22-32 nM) to compound 31 (8.5 nM).

Example 7—Metabolism Assays

Madin Darby Canine Kidney (MDCK) P-Glycoprotein Permeability Assays

The transcellular permeability of test compounds and the influence of Pgp-mediated efflux on drug permeability was assessed using hMDR1-MDCK monolayers grown on filter supports.

All compounds were dissolved in 100% DMSO to provide 10 mM stock solutions from which donor (dose) solutions were prepared in DMEM to give a final drug concentration of 10 μM. All dose solutions contained 10 μM propranolol as an internal standard.

hMDR1-MDCK seeded filters were exposed to a fixed volume of the donor solution containing the compound of interest and its ability to traverse the monolayer and appear in the receiver compartment measured over a 30 minute period at 37° C. Bidirectional permeability measurements were derived by examining the transfer of compound in both the apical to basolateral compartment, and vice versa. Sample analysis was conducted using LC-MS/MS with the detection settings optimised for each test compound.

Following analysis of the samples the apparent permeability coefficient (Papp, cm/sec) for the discovery compounds is determined using the following relationship:

$$P_{app} = \frac{V_R \times \Delta C_R}{A \times C_D \times \Delta t}$$

$V_R$=Volume of the receiver compartment

A=Surface area of the filter $C_D$=Drug concentration in the donor concentration Δt=incubation time $\Delta C_R$=the amount of drug detected in the receiver compartment The efflux ratio can be determined from these values by calculating the ratio of the Papp values derived in the B-A direction and A-B direction (i.e. Papp B-A/Papp A-B). If the resulting value is greater than 1.5 this is usually indicative of an efflux component (e.g. P-gp) influencing transport.

In Vitro Metabolic Studies

Microsomes are vesicles of endoplasmic reticulum isolated from liver homogenate following differential centrifugation. They contain drug metabolising enzymes including the cytochromes P450 (CYP) responsible for a majority of drug metabolism. They also contain the phase II metabolising enzyme responsible for glucuronidation—uridine diphosphate glucuronyltransferase (UDPGT). As they contain many of the drug metabolizing enzymes found in the liver they are useful in vitro models of hepatic clearance. Assays are performed by incubating drugs of interest at a concentration of 1 μM with the microsomes at 37° C. The disappearance of the test compound is monitored at fixed points over a period of 60 minutes and samples analysed using LC-MSMS. The resulting data can be used to determine:

1. Intrinsic clearance. These values can be used to categorise compounds into bands of high, medium or low clearance. Generally compounds with high clearances are considered to be less favourable as they are likely to be cleared more rapidly in vivo resulting in a short duration of action.
2. Rank order compounds in order of microsomal stability by calculating half-life.

Cytochrome Profiling

Cytochrome P450 (abbreviated CYP, P450 or CYP450) belong to very large and diverse superfamily of haemoproteins which accept both exogenous and endogenous compounds as substrates in enzymatic reactions and play a major role in drug metabolism. Although this class has more than 50 enzymes just 5 of them (CYP1A2, CYP2C9, CYP2C19, CYP2D6 and CYP3A4) are able to metabolise almost 90% of all drugs. Inhibition of these enzymes is one of the major reasons for drug-drug interactions. Consequently, detailed CYP inhibition profiles are a regulatory requirement for all new drugs.

Inhibition potencies against the five most relevant CYP isoforms is performed using baculosomes; microsomes prepared from insect cells infected with recombinant baculovirus containing cDNA for a specific human P450 isozyme. The baculosomes are incubated with drug at a concentration of 1 μM in the presence of a probe substrate for 60 minutes at 37° C. The probe is normally metabolised by the baculosomes to produce a fluorescent metabolite. A substrate drug will compete for the isozyme and reduce the metabolism of the probe resulting in a decrease in the fluorescent signal.

The percent inhibition due to the presence of the test compound is calculated using the following equation:

$$\% \text{ Inhibition} = \left(1 - \frac{X - B}{A - B}\right) \times 100\%$$

X=fluorescent intensity observed in the presence of test compound

A=fluorescent intensity observed in control

B=fluorescent intensity observed in the presence of the probe control

The metabolism data is presented in Table 3.

TABLE 3

Metabolism data for fluorinated compounds

| | | 31 | 3 | 2 | 1 |
|---|---|---|---|---|---|
| $P_{app}$[a] ($\times 10^{-6}$ cm/sec) | A-B | 40.9 | 28.1 | 40.0 | 30.3 |
| | B-A | 23.6 | 34.3 | 54.8 | 44.2 |
| Liver microsome[b] $T_{1/2}$ (h) | | 0.13 | 0.08 | 0.30 | 0.78 |
| CYP Profiling[c] (% inhibition with 10 μM substrate) | 1A2 | 25.68 | 7.86 | 7.04 | 5.48 |
| | 2C9 | 74.97 | 32.33 | −3.00 | 9.26 |
| | 2C19 | 84.43 | 46.91 | 1.50 | 12.90 |
| | 2D6 | −47.26 | −28.95 | −25.29 | −29.14 |
| | 3A4 | 84.43 | 88.75 | 89.88 | 89.93 |

[a]$P_{app}$ values were mean values (n = 3) ± standard deviation derived from bi directional transcellular permeability assay using Madin-Darby canine kidney (MDCK) cells.
[b]Half-lives were calculated using the gradient derived from plotting compound stability against time with n = 3 at each time point.
[c]Cytochrome P450 isozyme inhibition values were mean (n = 3) ± SEM In the rat liver microsome stability study compound 1 exhibited the greatest stability with a half-life 6 times longer than compound 31. A similar trend was observed in the CYP profile studies whereby the fluorinated benzamides 1, 2 and 3 encountered less CYP enzyme interactions (with the exception of CP3A4) than compound 31, with compound 1 performing the best.

It is apparent that fluorination of the bridgehead carbons of the adamantane moiety not only improves the physicochemical properties, but also hinders the main metabolic pathway which has resulted in metabolically more stable compounds.

Example 8—Pharmacokinetic Assays

Plasma Protein and Brain Tissue Binding Assays

Determining the extent to which a molecule binds to factors present within plasma and brain is a critical phase of drug development as this determines not only the free unbound fraction available to exert the desired pharmacological actions but also influences dosing, clearance rate and the potential for drug-drug interactions. Binding is measured with the rapid equilibrium dialysis technique using cartridges consisting of two compartments (sample and buffer chamber) separated by a dialysis membrane.

All compounds are prepared in 100% DMSO to provide 10 mM stock solutions. Sample material is prepared by spiking a known volume of plasma or brain with the stock solution such that the final concentration of compound is 1 μM. This is placed in the sample chamber of the dialysis cartridge. Dialysis buffer is then added to the buffer chamber and the cartridge incubated at 37° C. for 4 hours. Following the incubation the test compound concentrations are determined in the two chambers and the % free or bound component calculated using the equation below:

$$\% \text{ Free} = \frac{\text{Concentration in buffer chamber}}{\text{Concentration in sample chamber}} \times 100$$

$$\% \text{ Bound} = 100\% - \% \text{ Free}$$

In Vivo Pharmacokinetic Studies

Male Hans Wistar rats were purchased from Charles River Laboratories UK. During the acclimatisation period the rats were group housed in cages of three and maintained under a 12 hour light/dark cycle with free access to food and water. Temperature and humidity were controlled according to UK Home Office regulations.

All compounds were formulated immediately prior to dosing in 10% DMSO, 20% Cremophor EL, 70% saline to provide 1 mg/ml solutions. Each rat received a weight corrected dose of formulated drug at 1 mg/kg administered by intravenous bolus injection via a lateral tail vein.

Terminal plasma and brain samples were collected from n=3 animals at specified time points (0.017, 0.083, 0.25, 0.5, 1, 2, 4 and 6 hours following dose administration).

Drug quantification was performed using liquid chromatography-tandem mass spectrometry using electrospray ionisation. Pharmacokinetic parameters were calculated using Phoenix WinNonlin software.

The results are presented below in Table 4.

TABLE 4

Pharmacokinetic data for fluorinated compounds

| | 31 | | 3 | | 2 | | 1 | |
|---|---|---|---|---|---|---|---|---|
| Tissue | Plasma | Brain | Plasma | Brain | Plasma | Brain | Plasma | Brain |
| pb[a] (% bound) | 99.21 | 99.73 | 94.03 | 96.91 | 88.46 | 91.50 | 89.53 | 94.51 |
| $T_{1/2}$ (h) | 0.47 | 0.16 | 0.43 | 0.43 | 0.47 | 0.59 | 1.72 | 1.26 |
| $T_{max}$ (h) | 0.02 | 0.02 | 0.02 | 0.02 | 0.02 | 0.02 | 0.02 | 0.02 |
| $C_{max}$ (ng/mL) | 1190 | 1696 | 1265 | 2422 | 1716 | 1838 | 1289 | 1464 |
| $AUC_6$ (h * ng/mL) | 185.97 | 221.46 | 174.99 | 286.32 | 195.53 | 209.02 | 385.01 | 380.46 |
| $AUC_\infty$ (h * ng/mL) | 191.79 | 245.91 | 178.42 | 290.73 | 199.49 | 216.77 | 398.64 | 385.56 |
| Cl (mL/min/kg) | 86.90 | 67.78 | 93.41 | 57.33 | 83.55 | 76.89 | 41.81 | 43.23 |
| $V_d$ (L/kg) | 2.09 | 0.77 | 1.80 | 0.92 | 1.41 | 1.54 | 2.75 | 2.10 |

[a]Brain and plasma protein binding values were mean (n = 3) ± SEM with tissue and blood pooled from rats Compound 1 displayed superior results. All four compounds achieved equivalent maximum concentrations ($C_{max}$ 4-7 mM) in the brain that equated to over 100 times their binding affinity. However, all three fluorinated benzamides exhibited a higher percentage of unbound drug, in both plasma and brain, than compound 31. In the brain, the distribution of benzamides increases proportional to the amount of fluorine atoms present on adamantane with the volume of distribution ($V_d$) for compound 1 determined to be 3 times greater than compound 31. Analyzing the elimination data, compound 1 exhibits enhanced metabolic stability over all other benzamides of the series (consistent with the rat liver microsome results (Table 3)), with a plasma and brain half-life ($T_{1/2}$) of 3.7 and 7.9 (respectively) times longer than compound 31. The improved metabolic stability of compound 1 resulted in an improved drug exposure profile (AUC) which was almost twice that of all other benzamides in the series.

Example 9—Single Nucleotide Polymorphism Assays

Background

In humans, the $P2X_7R$ is highly polymorphic with the current Build of the NCBI database (Build 141) reporting 299 amino acid altering mutations in hP2X7R, of which 11 have a minor allele frequency above 1% (defined as a single nucleotide polymorphism (SNP)). Many studies are linking $P2RX_7R$ polymorphisms to various disease states.[4] It is therefore important that any potential drug lead also be effective against disease-inducing polymorphisms. The inhibitory potency of compound 1 against six functionally characterized hP2X7R SNPs which are known to cause either gain-of-function or no change in function of hP2X7R is investigated below.

General Experimental

HEK293 cells were cultured in DMEM/F12 supplemented with 10% heat inactivated fetal bovine serum, penicillin (100 U/ml) and streptomycin (100 U/ml). Cells were cultured in 25 $cm^2$ flasks and incubated at 37° C. in a 5% $CO_2$, humidified atmosphere and maintained in a log phase of growth by subculturing subconfluent cultures with trypsin every 3-4 days.

Transfection and Measurement of P2X7 Pore Function by Ethidium Bromide Uptake Assay Subconfluent cells were transiently transfected with mutated $P2X_7$ constructs using Lipofectamine 2000 (Invitrogen). After 24 h, cells were re-plated into alternate wells of pre-coated poly-D-Lysine 96-well plates at a density of $5\times10^4$ cells/well.

Following overnight incubation, cells were pre-treated in triplicate with various concentrations of compound 1 (1 nM-1 µM) in culture medium for 30 min at 37° C. in 5% $CO_2$, humidified atmosphere. The drug treated culture medium was then replaced with warmed assay buffer (145 mM NaCl, 10 mM Hepes, 13 mM glucose, 2 mM KCl, 0.2 mM $CaCl_2$, pH 7.3 with 25 µM ethidium bromide) supplemented with the same drug concentrations. Cellular uptake of ethidium bromide in response to either 1 mM ATP or 100 uM BzATP was measured at 37° C. using a FluoStar Optima fluorescence plate reader (BMG Labtech) with data read at $\lambda\ Ex_{544nm}/\lambda Em_{590nm}$ at 31 sec intervals over 60 cycles.

$P2X_7$ function was determined as the slope of the linear portion of the uptake curve and normalized against the response to ATP or BzATP in the absence of drug. $IC_{50}$ values were determined from the dose response curves derived from a four-parameter variable slope using GraphPad Prism 5. $IC_{50}$ values reported are the average of n=2 or 3 separate transfections.

The results are shown below in Table 5.

TABLE 5

Activity of compound 1 in the presence of $hP2X_7R$ SNPs.

| AA | | % WT | $IC_{50}$ (nM)[a] | |
|---|---|---|---|---|
| Change | Frequency[5] | Function | 1 mM ATP | 100 µM BzATP |
| WT | | | 49 ± 24 | 33 ± 6 |
| V76A | 0.062 | 44%[5] | ND | 24 ± 9 |
| H155T | 0.439 | 195%[5] | 49 ± 21 | 20 ± 5 |
| H270R | 0.255 | 195%[5] | 34 ± 17 | 52 ± 20 |
| A348T | 0.400 | >100%[6] | 48 ± 6 | 30 ± 10 |

TABLE 5-continued

| Activity of compound 1 in the presence of $hP2X_7R$ SNPs. | | | | |
|---|---|---|---|---|
| AA | | % WT | $IC_{50}$ (nM)[a] | |
| Change | Frequency[5] | Function | 1 mM ATP | 100 μM BzATP |
| T357S | 0.083 | 41%[7] | ND | 35 ± 12 |
| Q460R | 0.170 | 73% | 55 ± 4[b] | 62 ± 16[b] |

[a]$IC_{50}$ values were the mean values (n = 2-3 transfections) ± standard deviation derived from a dye uptake assay against ATP (1 mM) or BzATP (100 μM) with HEK293 cells transiently transfected with plasmids of functional $P2X_7R$ SNP variants.
[b]Plasmid contains 348T and 460R The results show that compound 1 is well tolerated against the relevant SNPs with little to no loss of inhibitory activity, suggesting a potential to modulate $P2X_7R$ activity in diseases states involving polymorphisms.

Example 10—IL-1β Inhibition

Background

The role of inflammation in cardiovascular disease processes was explored. Patients that were admitted to the Royal North Shore Hospital, Sydney, Australia for clinically indicated cardiac catheterisation were consented for the study. These patients were subdivided according to their clinical presentation:

1. Patients presenting with STEMI, characterised by recent-onset chest pain, ECG changes and/or raised cardiac enzymes.
2. Age and sex-matched control patients with no evidence of coronary stenosis on angiography.

Patients were excluded from the study if they were taking anti-inflammatory medications, or if they had clinical or biochemical evidence of active infection or inflammation.

Preparation of Patient-Derived Monocytes 20 mL of blood was collected from the arterial sheath into an EDTA-coated tube. Samples were immediately diluted 1:1 in phosphate buffered saline (PBS) and layered on top of Ficoll-Paque for gradient separation. Samples were centrifuged at 3000 g for 15 minutes. Peripheral blood mononuclear cells (PBMCs) were collected from the buffy coat layer and were washed with Dulbecco's PBS, centrifuged at 3000 g for 10 minutes, and a cell count performed using a haemocytometer. Isolated PBMCs were resuspended in RPMI-1640 cell culture media and seeded on a 48-well plate at $1.6\times10^5$ cells/well and 12-well plate at $5\times10^5$ cells/well. After 3 hours, cells were incubated with 1 μmol/L of compound 1 or vehicle-control (DMSO) for 30 minutes. Cells were then stimulated with 100 μmol/L Bz-ATP for 30 minutes or remained unstimulated. The monocyte supernatant and adherent monocyte cells were collected and stored for further analysis.

Dose-Response Testing in THP-1 Monocytic Cell Line

Figure 6:
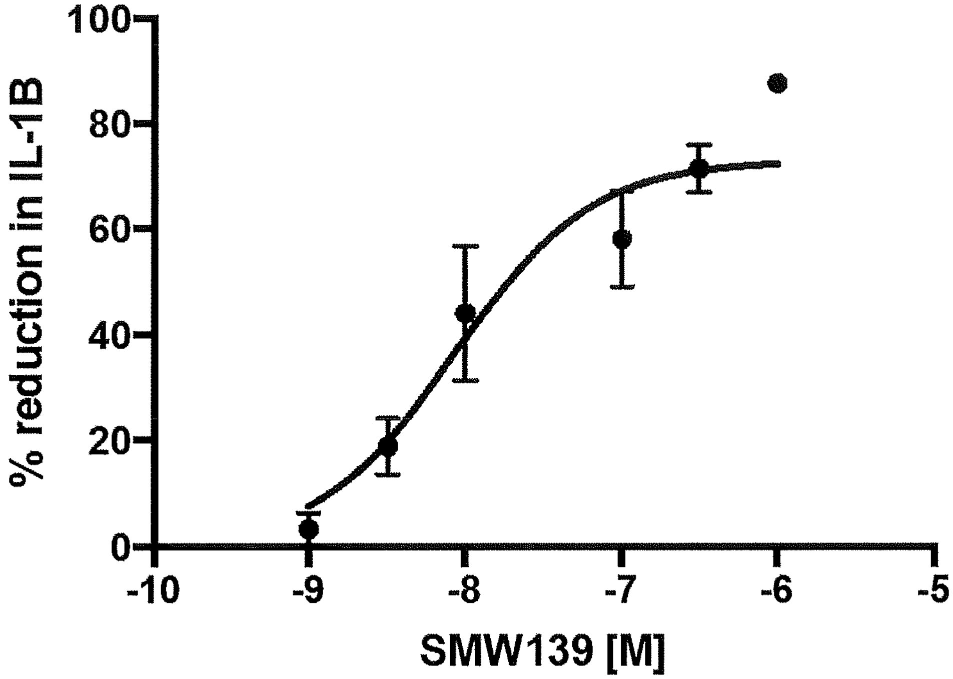
FIG. 6: Compound 1 dose-response curve. THP-1 monocytic cells were treated with interferon-γ and lipopolysaccharide for 3 hours, then pre-incubated with compound 1 (denoted as "SMW139", 1-1000 nM), prior to ATP stimulation to activate the inflammasome. Supernatant was collected to measure the level of secreted IL-1β. Sigmoidal dose-response curve demonstrated a LogEC50 of 8.069±0.16.

THP-1 monocytic cells were cultured in RPMI-1640 (0.05 mM 2-mercaptoethanol and 10% foetal bovine serum) in Corning T-75 flasks and sub-cultured when cell concentration reached $8\times10^5$ cells/mL as per manufacturer's instructions. Cells were plated in 48-well Corning cell-bind plates at $2\times10^5$ cells/well, and treated with recombinant human interferon-γ (10 ng/mL) and lipopolysaccharide (25 ng/mL) for 3 hours. Cells were then pre-incubated with compound 1 (1 nmol/L-1 μmol/L), prior to 1 uM Bz-ATP stimulation to activate the inflammasome. Supernatant was collected to measure the level of secreted IL-1ß. The results are shown in FIG. 6.

Inflammatory Signalling Measurements in Monocytes

Following sample preparation as outlined above, the following inflammatory markers were measured: IL-1B ELISA Changes in secreted and intracellular levels of IL-1β were measured by ELISA (RnD systems). Samples were diluted 1 in 2 in commercial diluent, assayed according to manufacturer's instructions and detected at 450/570 nm.

Figure 7:
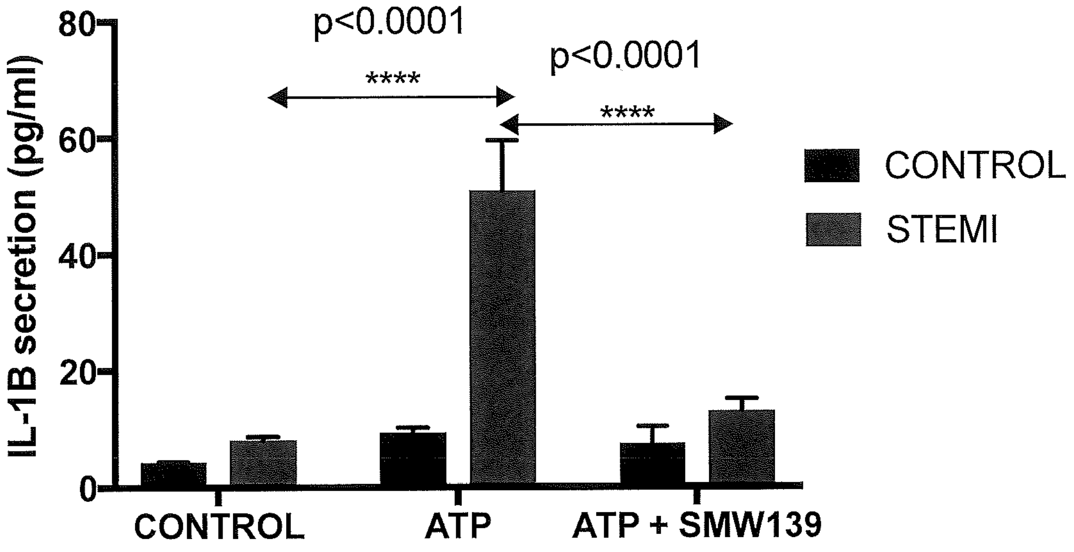
FIG. 7: Compound 1 in ST-Elevation Myocardial Infarction (STEMI) peripheral blood mononuclear cells (PBMCs).

Peripheral blood mononuclear cells (PBMCs) were collected from 19 STEMI patients at the time of infarct, and 3 healthy controls. Monocytes were pre-incubated with compound 1 (referred to as "SMW139") or DMSO control prior to ATP stimulation. IL-1β levels were measured by ELISA. Baseline levels of secreted IL-1β were significantly elevated in PBMCs from STEMI patients compared with healthy controls (STEMI: 8.2±0.6, Control: 4.2±0.1;p=0.02). There was a significant increase in IL-1β secretion post ATP-induced inflammasome activation in STEMI PBMCs (53.8±9.4;p<0.0001) but not control (9.8±0.9). $P2X_7$ inhibition significantly attenuated this ATP-induced IL-1β secretion in STEMI cells (13.9±2.4;p<0.0001) but had no effect in controls (7.5±2.8). See FIG. 7.

In summary, the most promising compound is compound 1 which demonstrated potent $P2X_7R$ inhibition, optimal physicochemical parameters, superior metabolic stability (ten times longer than compound 31), an improved physicokinetic profile and efficacy in the presence of several known $P2X_7R$ polymorphisms.

REFERENCES

1. Haky, J. E.; Young, A. M., Evaluation of a Simple HPLC Correlation Method for the Estimation of the Octanol-Water Partition Coefficients of Organic Compounds. *J. Liq. Chromatogr.* 1984, 7 (4), 675-689
2. Sangster, J., Octanol-Water Partition Coefficients of Simple Organic Compounds. *Journal of Physical and Chemical Reference Data* 1989, 18 (3), 1111-1229.
3. Humphreys, B. D.; Dubyak, G. R., Induction of the $P2z/P2X_7$ nucleotide receptor and associated phospholipase D activity by lipopolysaccharide and IFN-gamma in the human THP-1 monocytic cell line. *Journal of immunology* (*Baltimore, Md.:* 1950) 1996, 157 (12), 5627-37.
4. (a) Gu, B. J.; Field, J.; Dutertre, S.; Ou, A.; Kilpatrick, T. J.; Lechner-Scott, J.; Scott, R.; Lea, R.; Taylor, B. V.; Stankovich, J.; Butzkueven, H.; Gresle, M.; Laws, S. M.; Petrou, S.; Hoffjan, S.; Akkad, D. A.; Graham, C. A.; Hawkins, S.; Glaser, A.; Bedri, S. K.; Hillert, J.; Matute, C.; Antiguedad, A.; Wiley, J. S.; Baxter, A. G.; Kermode, A. G.; Taylor, B. V.; Booth, D. R.; Mason, D. F.; Stewart, G. J.; Butzkueven, H.; Charlesworth, J. C.; Wiley, J. S.; Lechner-Scott, J. S.; Field, J.; Tajouri, L.; Griffiths, L. R.; Slee, M.; Brown, M. A.; Moscato, P.; Scott, R. J.; Broadley, S. A.; Vucic, S.; Kilpatrick, T. J.; Carroll, W. M.; Barnett, M. H., A rare $P2X_7$ variant Arg307Gln with absent pore formation function protects against neuroinflammation in multiple sclerosis. *Hum. Mol. Genet.* 2015, 24 (19), 5644-5654; (b) Gartland, A.; Skarratt, K. K.; Hocking, L. J.; Parsons, C.; Stokes, L.; Jorgensen, N. R.; Fraser, W. D.; Reid, D. M.; Gallagher, J. A.; Wiley, J. S., Polymorphisms in the $P2X_7$ receptor gene are associated with low lumbar spine bone mineral density and accelerated bone loss in post-menopausal women. *Eur. J. Hum. Genet.* 2012, 20 (5), 559-564.
5. Stokes, L.; Fuller, S. J.; Sluyter, R.; Skarratt, K. K.; Gu, B. J.; Wiley, J. S., Two haplotypes of the $P2X_7$ receptor containing the Ala-348 to Thr polymorphism exhibit a gain-of-function effect and enhanced interleukin-1β secretion. *FASEB J.* 2010, 24 (8), 2916-2927.

6. Sun, C.; Chu, J.; Singh, S.; Salter, R. D., Identification and characterization of a novel variant of the human $P2X_7$ receptor resulting in gain of function. *Purinergic Signal.* 2010, 6 (1), 31-45.

7. Shemon, A. N.; Sluyter, R.; Fernando, S. L.; Clarke, A. L.; Dao-Ung, L. P.; Skarratt, K. K.; Saunders, B. M.; Tan, K. S.; Gu, B. J.; Fuller, S. J.; Britton, W. J.; Petrou, S.; Wiley, J. S., A Thr357 to Ser polymorphism in homozygous and compound heterozygous subjects causes absent or reduced P2X7 function and impairs ATP-induced mycobacterial killing by macrophages. *J Biol Chem* 2006, 281 (4), 2079-86.

The citation of any reference herein should not be construed as an admission that such reference is available as prior art to the present application. Further, the reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavour to which this specification relates.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps, features, compositions and compounds.

The invention claimed is:

1. A compound of the general formula (I):

(I)

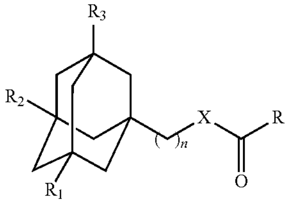

or a pharmaceutically acceptable salt, hydrate, derivative, solvate, or tautomer thereof, wherein:

$R_1$, $R_2$ and $R_3$ are independently selected from the group consisting of: hydrogen, hydroxy and halogen;

n is an integer between 0 and 4;

X is selected from the group consisting of: NH, O and S;

R is:

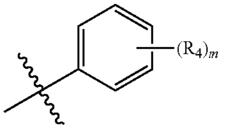

wherein each $R_4$ is independently selected from the group consisting of: halogen, hydroxy, methoxy and amino; and m is 2, with the proviso that at least one of $R_1$, $R_2$ and $R_3$ is F.

2. The compound of claim 1, wherein $R_1$, $R_2$ and $R_3$ are independently selected from hydrogen and halogen.

3. The compound of claim 2, wherein $R_1$, $R_2$ and $R_3$ are all F.

4. The compound of claim 1, wherein n is an integer between 1 and 4.

5. The compound claim 1, wherein X is NH.

6. The compound of claim 1, wherein each $R_4$ is independently selected from the group consisting of: halogen, hydroxy and methoxy.

7. The compound of claim 1, wherein one $R_4$ is methoxy and the other $R_4$ is Cl.

8. The compound according to claim 1, wherein R is selected from the group consisting of:

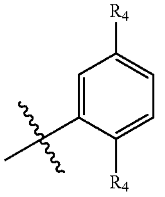

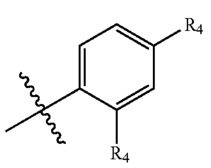

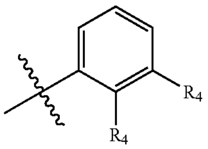

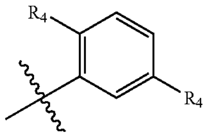

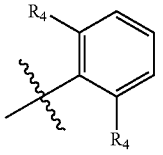

.

9. The compound according to claim 1, wherein R is selected from the group consisting of:

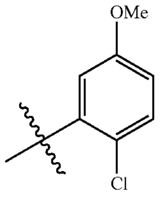

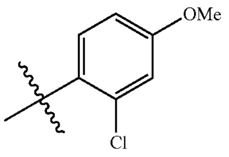

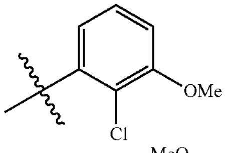

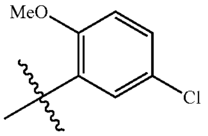

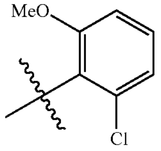

.

10. A compound according to claim 1 having a structure selected from the group consisting of:

1
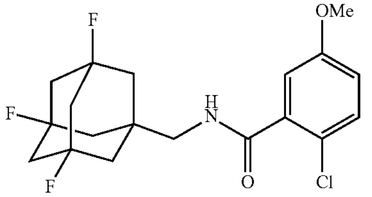
2
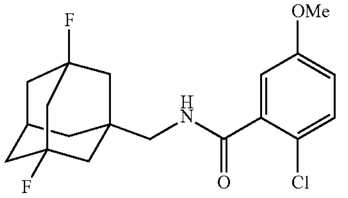
3
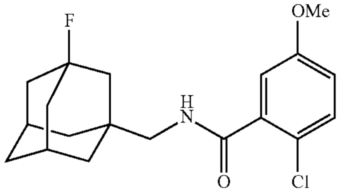
4
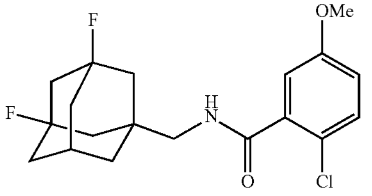
5
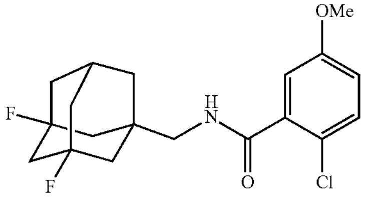
6
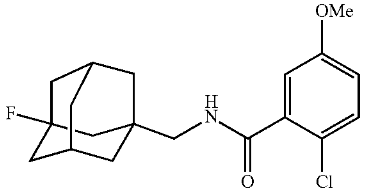
7
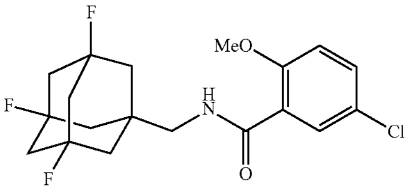
8
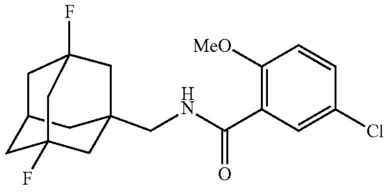
-continued
9
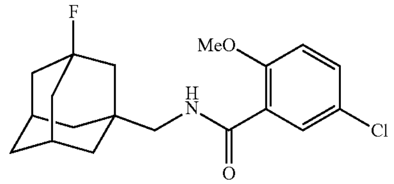
10
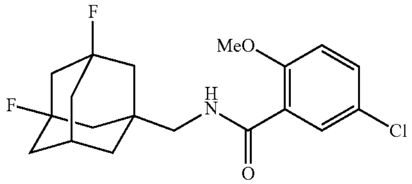
11
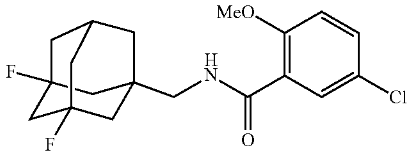
12
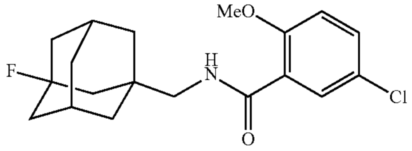
13
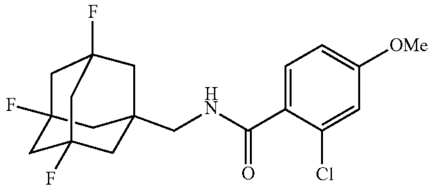
14
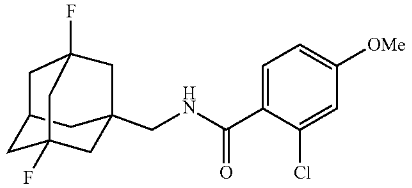
15
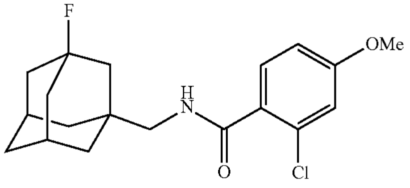
16
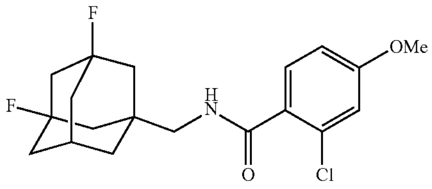

-continued
17
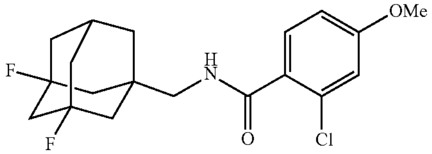
18
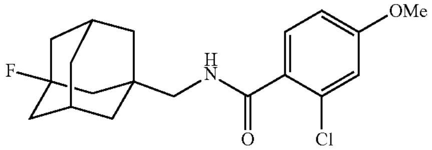
19
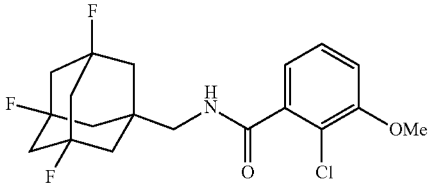
20
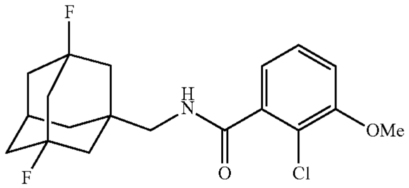
21
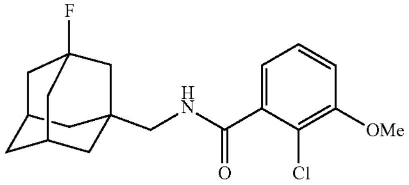
22
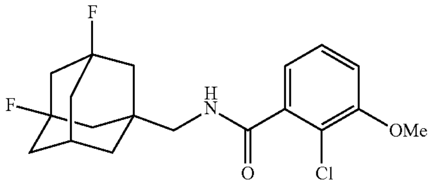
23
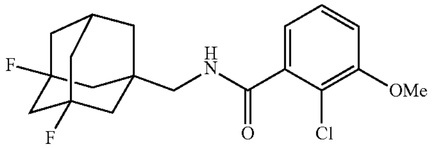
24
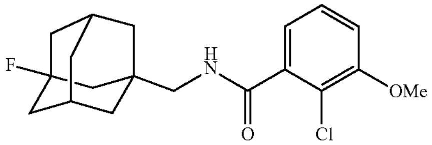
25
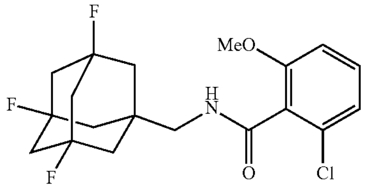
-continued
26
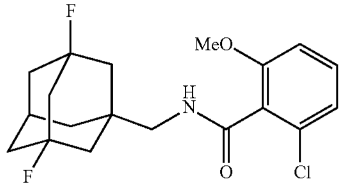
27
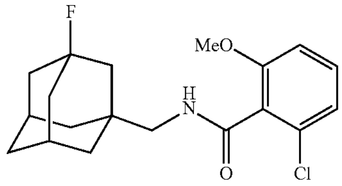
28
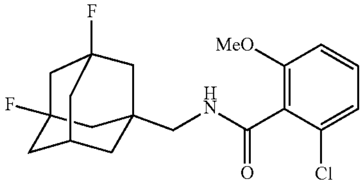
29
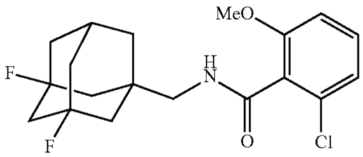
30
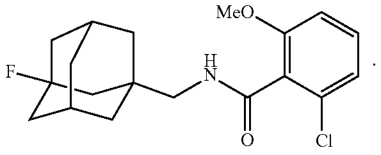
11. A compound of claim 1, having a structure
1
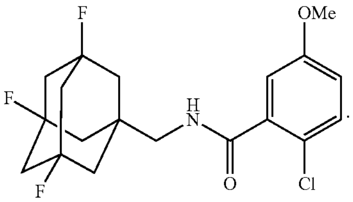
12. A pharmaceutical composition comprising a compound of formula (I) according to claim 1, together with a pharmaceutically acceptable carrier, diluent or excipient.
* * * * *